United States Patent
Hamilton et al.

(10) Patent No.: US 7,141,560 B2
(45) Date of Patent: Nov. 28, 2006

(54) ALANINE 2,6-DIALKOXYPHENYL ESTER DERIVATIVES AS HYPNOTICS

(75) Inventors: Niall Morton Hamilton, Newhouse (GB); David Jonathan Bennett, Newhouse (GB)

(73) Assignee: Akzo Nobel N.V., Arnhem (NL)

( * ) Notice: Subject to any disclaimer, the term of this patent is extended or adjusted under 35 U.S.C. 154(b) by 343 days.

(21) Appl. No.: 10/466,805

(22) PCT Filed: Jan. 17, 2002

(86) PCT No.: PCT/EP02/00994

§ 371 (c)(1),
(2), (4) Date: Jul. 18, 2003

(87) PCT Pub. No.: WO02/057218

PCT Pub. Date: Jul. 25, 2002

(65) Prior Publication Data

US 2004/0059109 A1  Mar. 25, 2004

(30) Foreign Application Priority Data

Jan. 19, 2001  (EP) .................................. 01200195

(51) Int. Cl.
*A61K 31/221* (2006.01)
*A61K 31/553* (2006.01)
*A61K 31/54* (2006.01)
*C07C 267/10* (2006.01)
*C07C 207/06* (2006.01)

(52) U.S. Cl. .......................... 514/211.01; 514/217.12; 514/227.5; 514/227.8; 514/237.8; 514/239.2; 514/316; 514/317; 514/327; 514/428; 540/450; 540/544; 540/610; 544/60; 544/59; 544/158; 544/168; 544/171; 544/111; 544/128; 548/573; 546/216; 546/238; 546/249; 560/130

(58) Field of Classification Search ........... 514/211.01; 540/450; 544/59; 546/216; 548/573; 560/130
See application file for complete search history.

(56) References Cited

FOREIGN PATENT DOCUMENTS

| | | | |
|---|---|---|---|
| GB | 1 102 011 A | 2/1968 | |
| GB | 1 160 468 | 8/1969 | |
| WO | 00 05196 A | 2/2000 | |

OTHER PUBLICATIONS

Brancaccio, G. et al., "Anestetici Locali," Il Farmaco, Ed. Sc., vol. 19 (1964) pp. 986-1002.
Zimmerman, S. A. et al., "Potentiation of γ-Aminobutyric Acid$_A$ Receptor Cl$^{15}$ Current Correlates with *In Vivo* Anesthetic Potency[1]," J. Pharmacol. Exp. Therap., vol. 270, No. 3 (1994) pp. 987-991.
Franks, N. P. et al., "Molecular and cellular mechanisms of general anaesthesia," Nature, vol. 367 (1994), pp. 607-613.
Tanelian, D. L. et al., "The Role of the GABA$_A$ Receptor/Chloride Channel Complex in Anesthesia," Anesthesiology, vol. 78, No. 4 (1993) pp. 757-776.

*Primary Examiner*—Kamal A. Saeed
*Assistant Examiner*—Jason M. Nolan
(74) *Attorney, Agent, or Firm*—Susan Hess; David H. Vickrey; F. Aaron Dubberley

(57) ABSTRACT

The present invention relates to alanine 2,6-dialkoxyphenyl ester derivatives having the general formula I

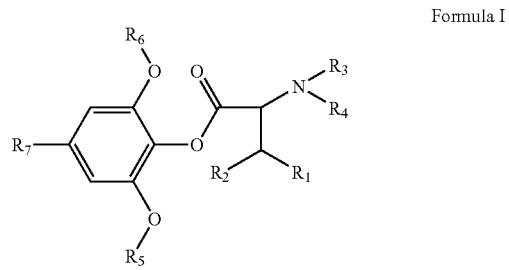

Formula I The invention also relates to pharmaceutical compositions comprising said derivatives, and to the use of these alanine 2,6-dialkoxyphenyl ester derivatives as hypnotics for the induction and maintenance of general anaesthesia.

14 Claims, No Drawings

ALANINE 2,6-DIALKOXYPHENYL ESTER DERIVATIVES AS HYPNOTICS

This application is a National Stage of International Application No. PCT/EP02/00994, filed Jan. 17, 2002.

The invention relates to alanine 2,6-dialkoxyphenyl ester derivatives, to pharmaceutical compositions containing the same, as well as to the use of these alanine 2,6-dialkoxyphenyl ester derivatives as hypnotics for the induction and maintenance of general anaesthesia.

It has been reported (G. Brancaccio and A. Larizza, II Farmaco 1964, 19, 986–1002) that alanine 2,6-dialkoxyphenyl ester derivatives, wherein the amino group is either dialkylated or is part of an heterocyclic system (GB 1,102, 011: Richardson-Merrell S.p.A.), possess local anaesthetic activity, with piperazinyl derivatives proving the most active. In GB 1,160,468 (May & Baker Ltd.) an alanine 2,6-dialkoxyphenyl ester derivative wherein the amino group is part of a morpholinyl ring, i.e. 2,6-dimethoxyphenyl 2-morpholinopropionate, is disclosed as an intravenous general anaesthetic having a short duration of activity with rapid, smooth recovery. The hypnotic properties of this compound are attained at rather high dose levels and consequently there exists a need for water soluble general anaesthetics with improved potency.

The present invention provides alanine 2,6-dialkoxyphenyl ester derivatives having the general formula I

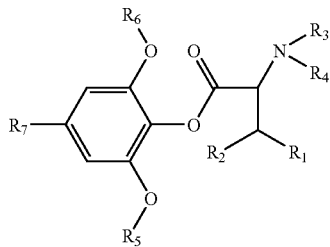

Formula I wherein
$R_1$ is $(C_{1-3})$alkyloxy, $(C_{1-3})$alkyloxy$(C_{1-3})$alkyl, $(C_{1-3})$alkylthio, $(C_{1-3})$alkylthio$(C_{1-3})$-alkyl, $(C_{1-3})$alkylsulfinyl, $(C_{1-3})$alkylsulfinyl$(C_{1-3})$alkyl, $(C_{1-3})$alkylsulfonyl, $(C_{1-3})$alkylsulfonyl$(C_{1-3})$alkyl, $(C_{1-3})$alkyloxycarbonyl, $(CH_2)_n$—CO—$NR_8R_9$ or $(CH_2)_n$—$NR_8R_9$;
n is 0, 1 or 2;
$R_2$ is hydrogen or $(C_{1-3})$alkyl;
$R_3$ is $(C_{1-3})$alkyl or $(C_{1-3})$alkyloxy$(C_{1-3})$alkyl;
$R_4$ is $(C_{1-3})$alkyloxy$(C_{1-3})$alkyl; or
$R_3$ and $R_4$ form together with the nitrogen atom to which they are bound a 5-, 6-, or 7-membered ring, optionally containing a further heteroatom selected from O and S, and which ring may optionally contain a double bond and be optionally substituted with $(C_{1-3})$alkyl or $(C_{1-3})$alkyloxy;
$R_5$ and $R_6$ are independently $(C_{1-3})$alkyl;
$R_7$ is hydrogen, $(C_{1-3})$alkyl, $(C_{1-3})$alkyloxy or $(C_{2-3})$alkenyl;
$R_8$ and $R_9$ are independently $(C_{1-3})$alkyl; or
$R_8$ and $R_9$ form together with the nitrogen atom to which they are bound a 5-, 6-, or 7-membered, optionally containing a further heteroatom selected from O and S, and which ring may optionally contain a double bond; or a pharmaceutically acceptable salt thereof.

The alanine 2,6-dialkoxyphenyl ester derivatives of formula I, having an amino group which is either dialkylated or is part of a heterocyclic ring system, were found to be potent intravenous hypnotics with quick onset, and a short duration of action with rapid, smooth recovery. Many of the compounds have the additional advantage of being highly water soluble.

The term $(C_{1-3})$alkyl, as used in the definition of formula I, means a branched or unbranched alkyl group having. 1–3 carbon atoms, like n-propyl, isopropyl, ethyl and methyl.

In the term $(C_{1-3})$alkyloxy as used in formula I, $(C_{1-3})$ alkyl has the meaning as previously given, preferably methyl.

The term $(C_{2-3})$alkenyl means an alkenyl group having 2 or 3 atoms, such as propen-2-yl (allyl), propen-1-yl or ethenyl (vinyl). Alkenyl groups having 3 carbon atoms may be in the E- or Z-form, or a mixture thereof.

In the definition of Formula I $R_3$ and $R_4$ may form together with the nitrogen atom to which they are bound a 5-, 6-, or 7-membered ring, optionally containing a further heteroatom selected from O and S, and which ring may optionally contain a double bond and be optionally substituted with $(C_{1-3})$alkyl or $(C_{1-3})$alkyloxy. Examples of such ring systems are hexahydro-1,4-oxazepine (homomorpholine), morpholine, thiomorpholine, hexahydroazepine (homopiperidine), pyrrolidine, piperidine, 1,2,3,6-tetrahydropyridine, 4-methoxypiperidine, 2,2-dimethylmorpholine, 2,2-dimethylthiomorpholine, 1,2,3,4-tetrahydroisoquinoline, 2-methylmorpholine, 2-ethylmorpholine, 2-isopropylmorpholine and the like. Preferred ring systems formed by $R_3$ and $R_4$ are hexahydro-1,4-oxazepine, morpholine and thiomorpholine.

In the definition of Formula I $R_1$, can be $(CH_2)_n$—CO—$NR_8R_9$ or $(CH_2)_n$—$NR_8R_9$, wherein n is 0, 1 or 2, and wherein $R_8$ and $R_9$ may form together with the nitrogen atom to which they are bound a 5-, 6-, or 7-membered, optionally containing a further heteroatom selected from O and S, and which ring may optionally contain a double bond. Examples of such ring systems are hexahydro-1,4-oxazepine, morpholine, thiomorpholine, pyrrolidine, piperidine, 1,2,3,6-tetrahydropyridine, 2,2-dimethylmorpholine and the like.

Preferred alanine 2,6-dialkoxyphenyl ester derivatives of the invention correspond to compounds having formula I wherein $R_5$ and $R_6$ is methyl. More preferred are the derivatives wherein $R_3$ and $R_4$ form together with the nitrogen atom to which they are bound form a 5-, 6- or 7-membered ring. Examples of such ring systems, as well as the preferred ones are as given above.

The compounds of formula I and their salts contain at least one centre of chirality, i.e. at the α-carbon atom, and exist therefore as stereoisomers, including enantiomers and, when appropriate, diastereomers. The present invention includes the aforementioned stereoisomers within its scope and each of the individual R and S enantiomers of the compounds of formula I and their salts, substantially free, i.e. associated with less than 5%, preferably less than 2%, in particular less than 1% of the other enantiomer, and mixtures of such enantiomers in any proportions including the, racemic mixtures containing substantially equal amounts or the two enantiomers.

Preferred are the alanine 2,6-dialkoxyphenyl ester derivatives of formula I wherein the configuration at the α-carbon atom is that of the R-enantiomer. Particular preferred compounds according to the invention, which have found to be useful as hypnotics for intravenous anaesthesia, are:

2R-[4-(hexahydro-1-oxazepinyl)]-3-methoxypropionic acid, 2,6-dimethoxyphenyl ester; and 2R-[4-(hexahydro-1-oxazepinyl)]-4-methoxybutyric acid, 2,6-dimethoxyphenyl ester γ-Aminobutyric acid (GABA) is the major inhibitory neurotransmitter within the central nervous system and it is probable that compounds potentiating the is effects of GABA at $GABA_A$ receptors will induce anaesthesia (S. A. Zimmerman, M. V. Jones and N. L. Harrison, J. Pharmacol. Exp. Therap. 1994, 270, 987–991; N. P. Franks and W. R. Lieb, Nature 1994, 367, 607–614). Indeed there is compelling evidence that many hypnotics exert their biological activity via modulation of $GABA_A$ receptors, including steroids, barbiturates, benzodiazepines and propofol (D. L. Tanelian, P. Kosek, I. Mody and M. B. MacIver, Anesthesiology 1993, 78, 757–776). The compounds of the present invention have been shown to modulate the specific binding of [$^{35}$S]-tertbutylbicyclophosphorothionate to rat whole brain membranes, consistent with allosteric modulation of $GABA_A$ receptors.

In addition to their general anaesthetic activity, the compounds of the invention can be used as sedative and analgesic drugs and in the treatment of GABA related diseases, such as anxiety, stress, sleep disorders, post natal depression, and premenstrual tension, and in the alleviation of seizure.

The invention also relates to pharmaceutical compositions comprising an alanine 2,6-dialkoxyphenyl ester derivative having the general formula I or a pharmaceutically acceptable salt thereof.

The compounds of the invention may be prepared by condensation of an appropriately $R_5,R_6,R_7$-substituted phenol, wherein $R_5$, $R_6$ and $R_7$ have the previously given meanings, with an activated acid derivative according to formula II

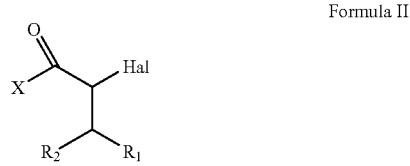

Formula II wherein $R_1$ and $R_2$ have the meanings as previously defined, Hal means halogen, and is selected from iodo, bromo or chloro, preferably bromo, and X is also halogen, preferably chloride, after which the resulting intermediate ester derivative of formula III

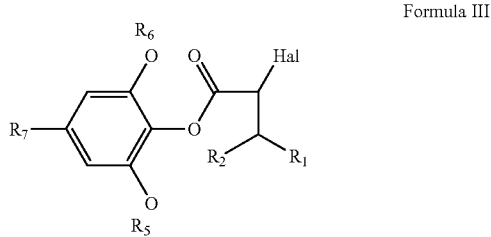

Formula III is reacted with an amine according to the formula $R_3R_4NH$, wherein $R_3$ and $R_4$ have the meanings as previously defined, optionally followed by conversion into a pharmaceutically acceptable salt.

The acid halogenide according to formula II, wherein X is halogen, can be prepared from the acid derivative according to formula II, wherein X is OH, by treatment with an inorganic acid halide, such as thionyl chloride, or an organic acid halide, such as oxalyl chloride. The intermediate acid derivative of Formula II, wherein X is OH, can be prepared using methods well known to the skilled person, for example by treatment of the corresponding α-amino acid, $NH_2$—CH$(CHR_1R_2)$—COOH with sodium nitrite in aqueous hydrobromic acid.

Alternatively the intermediate ester derivative of formula III may be prepared by condensation of an appropriately $R_5,R_6,R_7$-substituted phenol, wherein $R_5$, $R_6$ and $R_7$ have the previously given meanings, with an acid according to Formula II, wherein X is OH, and Hal is iodo, bromo or chloro, preferably bromo, with the aid of a condensing agent, such as bromo-trispyrrolidino-phosphonium hexafluorophosphate (PyBrop), dicyclohexylcarbodiimide/N-hydroxybenzotriazole and the like.

The compounds of the invention may also be prepared by condensation of an appropriately $R_5,R_6,R_7$-substituted phenol, wherein $R_5$, $R_6$ and $R_7$ have the previously given meanings, with an α-amino acid derivative according to the formula $R_3R_4N$—CH$(CHR_1R_2)$—$CO_2H$, wherein $R_1R_4$ have the previously given meanings, with the use of a condensation agent, such as those mentioned above.

The alanine 2,6-dialkoxyphenyl ester derivatives of Formula I contain at least one chiral carbon atom, i.e. the α-carbon atom. The compounds can therefore be obtained as pure stereoisomers, or as a mixture of stereoisomers. Methods for asymmetric synthesis whereby the pure stereoisomers are obtained are well known in the art, e.g. synthesis with chiral induction, enantioselective enzymatic ester hydrolysis, separation of stereoisomers or enantiomers using chromatography on chiral media. Such methods are for example described in *Chirality in Industry* (edited by A. N. Collins, G. N. Sheldrake and J. Crosby, 1992; John Wiley).

Pharmaceutically acceptable salts may be obtained by treating the free base of the compounds according to formula I with a mineral acid such as hydrochloric acid, hydrobromic acid, phosphoric acid, and sulphuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulphonic acid and the like.

The present invention further provides pharmaceutical compositions comprising an alanine 2,6-dialkoxyphenyl ester derivative having the general formula I, or a pharmaceutically acceptable salt thereof, in admixture with pharmaceutically acceptable auxiliaries, and optionally other therapeutic agents. The term "acceptable" means being compatible with the other ingredients of the composition and not deleterious to the recipients thereof. Compositions include e.g. those suitable for oral, sublingual, subcutaneous, intravenous, intramuscular, local, or rectal administration, and the like, all in unit dosage forms for administration. The intravenous route of administration is the preferred one when the hypnotic properties of the compounds of the invention are to be utilized for general anaesthesia.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro et al., Remington's Pharmaceutical Sciences, (18th ed., Mack Publishing Company, 1990, see especially Part 8: Pharmaceutical Preparations and Their Manufacture), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The compounds of the invention may be administered for humans in a dosage of 0.001–50 mg per kg body weight, preferably in a dosage of 0.1–20 mg per kg body weight.

The invention is illustrated by the following examples.

EXAMPLES

General.

Analysis of Compounds: The mass spectra of compounds of Formula I and their salts by electron spray ionisation (ESI) afford a parent ion that corresponds to the mass of the free base. While either the compound of Formula I or its salt may have been analysed by this method, the result is indicated below for the compound (and not the salt) in the following examples.

Example 1

1a: 2-Bromoacrylic acid, 2,6-dimethoxyphenyl ester.
   2,3-Dibromopropionyl chloride (30 g, 0.12 mol) and 2,6-dimethoxyphenol (18 g, 0.12 mol) were dissolved in anhydrous dichloromethane (800 ml) with stirring and cooling. Triethylamine (42 ml, 0.3 mol) was added dropwise over 1 h and the reaction mixture was left to stir for a further 3 h at room temperature. The solvent was removed under reduced pressure and diethyl ether (400 ml) added. The precipitate was then removed by filtration and the filtrate washed with water, dried over sodium sulphate, filtered and concentrated under reduced pressure to give the title compound (28 g, 81%) as a cream powder.
   $^1$H NMR (CDCl$_3$): δ 3.81 (s, 6H), 6.45 (s, 1H), 6.61 (d, 2H), 7.14 (t, 1H), 7.20 (s, 1H).

The following compound was prepared in a similar manner:

1b: 2-Bromoacrylic acid, 2,6-dimethoxy-4-methylphenyl ester.
   $^1$H NMR (CDCl$_3$): δ 2.34 (s, 3H), 3.79 (s, 6H), 6.39–6.44 (m, 3H), 7.19 (s, 1H).

Example 2

2a: 2-Bromo-3-methoxypropionic acid, 2,6-dimethoxyphenyl ester.
   2-Bromoacrylic acid, 2,6-dimethoxyphenyl ester (12 g, 42 mmol) was dissolved in methanol (300 ml, HPLC grade) and sodium methoxide (0.23 g, 4.2 mmol) added with stirring. The resultant solution was then stirred at room temperature for 30 minutes prior to the addition of ammonium chloride (0.5 g). The solvent was then removed under reduced pressure and diethyl ether (200 ml) added. The precipitate was removed by filtration and the filtrate evaporated under reduced pressure to give a yellow oil. Chromatography of this oil on silica using toluene as the eluent afforded the title compound (6.3 g, 48%) as a clear oil.
   $^1$H NMR (CDCl$_3$): δ 3.48 (s, 3H), 3.82 (s, 6H), 3.85–3.94 (m, 1H), 4.01–4.09 (m, 1H), 4.66 (t, 1H), 6.60 (d, 2H), 7.17 (t, 1H).

The following compound was prepared in a similar manner:

2b: 2-Bromo-3-methoxypropionic acid, 2,6-dimethoxy-4-methylphenyl ester.
   $^1$H NMR (CDCl$_3$): δ 2.33 (s, 3H), 3.47 (s, 3H), 3.79 (s, 6H), 3.82–3.91 (m, 1H), 4.00–4.08 (m, 1H), 4.63 (t, 1H), 6.41 (s, 2H).

Utilisation of sodium ethoxide and ethanol instead of sodium methoxide and methanol in the protocol described above afforded:

2c: 2-Bromo-3-ethoxypropionic acid, 2,6-dimethoxyphenyl ester.
   $^1$H NMR (CDCl$_3$): δ 1.24 (t, 3H), 3.64 (q, 2H), 3.82 (s, 6H), 3.85–3.94 (m, 1H), 4.05–4.13 (m, 1H), 4.62 (t, 1H), 6.58 (d, 2H), 7.14 (t, 1H).

Example 3

3a: 2-[4-(Hexahydro-1-oxazepinyl)]-3-methoxypropionic acid, 2,6-dimethoxyphenyl ester.
   2-Bromo-3-methoxypropionic acid, 2,6-dimethoxyphenyl ester (2.6 g, 8.2 mmol) was dissolved in toluene (30 ml) with stirring. Triethylamine (2.5 ml, 18.2 mmol) and hexahydro-1,4-oxazepine (1 g, 9.9 mmol) were then added and the reaction mixture heated at 100° C. under nitrogen overnight. The reaction mixture was then cooled to room temperature and diluted with diethyl ether (100 ml). The precipitate was removed by filtration and washed with diethyl ether (100 ml). The combined organic fractions were then extracted with 1N HCl (100 ml). The aqueous phase was subsequently basified to pH14 with 4M NaOH and extracted with diethyl ether (100 ml×2). The combined organic fractions were dried over sodium sulphate, filtered and concentrated under reduced pressure to give a yellow oil. Chromatography of this oil on basic alumina using toluene/ethyl acetate gradient as the eluent afforded the title compound (0.7 g, 26%) as a clear oil which crystallised on standing.
   Positive Ion ESI (M+H)$^+$ 339.9

The following compounds were prepared in a similar manner:

3b: 2-[N-Bis(2-methoxyethyl)amino]-3-methoxypropionic acid, 2,6-dimethoxyphenyl ester: Positive Ion ESI (M+H)$^+$ 372.2

3c: 3-Methoxy-2-[N-thiomorpholinyl]propionic acid, 2,6-dimethoxyphenyl ester: Positive Ion ESI (M+H)$^+$ 342.2

3d: 2-[N-(Hexahydroazepinyl)]-3-methoxypropionic acid, 2,6-dimethoxyphenyl ester: Positive Ion ESI (M+H)+ 337.8

3e: 3-Methoxy-2-[4-morpholinyl]propionic acid, 2,6-dimethoxyphenyl ester. Positive Ion ESI (M+H)+ 326.0

3f: 2-[N-Bis(3-methoxypropyl)amino]-3-methoxypropionic acid, 2,6-dimethoxyphenyl ester: Positive Ion ESI (M+H)+ 399.9

3g: 2-[N-Bis(3-ethoxyethyl)amino]-3-methoxypropionic acid, 2,6-dimethoxyphenyl ester: Positive Ion ESI (M+H)+ 400.2

3h: 3-Methoxy 2-[1-pyrollidinyl]propionic acid, 2,6-dimethoxyphenyl ester. Positive Ion ESI (M+H)+ 310.2

3i: 2-[N-Bis(2-methoxyethyl)amino]-3-methoxypropionic acid, 2,6-dimethoxy-4-methylphenyl ester: Positive Ion ESI (M+H)+ 386.2

3j: 3-Methoxy-2-[N-thiomorpholinyl]propionic acid, 2,6-dimethoxy-4-methylphenyl ester: Positive Ion ESI (M+H)+ 356.2

3k: 3-Methoxy-2-[4-morpholinyl]propionic acid, 2,6-dimethoxy-4-methylphenyl ester: Positive Ion ESI (M+H)+ 340.2

3l: 3-Methoxy-2-[N-(2-Methoxyethyl)methylamino]propionic acid, 2,6-dimethoxy-4-methylphenyl ester: Positive Ion ESI (M+H)+ 342.2

3m: 2-[4-(Hexahydro-1-oxazepinyl)]-3-methoxypropionic acid, 2,6-dimethoxy-4-methylphenyl ester: Positive Ion ESI (M+H)+ 354.0

3n: 3-Methoxy-2-[1-pyrrolidinyl]propionic acid, 2,6-dimethoxy-4-methylphenyl ester: Positive Ion ESI (M+H)+ 324.0

3o: 3-Methoxy-2-[1-piperidinyl]propionicacid, 2,6-dimethoxy-4-methylphenyl ester: Positive Ion ESI (M+H)+ 338.2

3p: 2-[N-Bis(3-methoxypropyl)amino]-3-methoxypropionic acid, 2,6-dimethoxy-4-methylphenyl ester: Positive Ion ESI (M+H)+ 414.4

3q: 2-[N-Bis(2-ethoxyethyl)amino]-3-methoxypropionic acid, 2,6-dimethoxy-4-methylphenyl ester: Positive Ion ESI (M+H)+ 414.0

3r: 3-Ethoxy-2-[4-(Hexahydro-1-oxazepinyl)]propionic acid, 2,6-dimethoxyphenyl ester: Positive Ion ESI (M+H)+ 353.7

Example 4

4a: 2-[N-Bis(2-methoxyethyl)amino]-3-methoxypropionic acid, 2,6-dimethoxy-4-methylphenyl ester.

Sodium ethoxide (0.2 g, 3 mmol) was added to a solution of 2-bromo-3-methoxypropionic acid, 2,6-dimethoxy-4-methylphenyl ester (8 g, 26.3 mmol) in ethanol (200 ml) and stirred at room temperature for 30 minutes. Ammonium chloride (0.32 g, 6 mmol) was then added and the solvent removed under reduced pressure. After removal of insoluble material by filtration, the solvent was removed under reduced pressure to give a clear oil. This oil was committed to further reaction without further purification. Bis-(2-methoxyethyl)amine (4.1 ml, 28 mmol) and triethylamine (4 ml, 28 mmol) were added to a solution of the product just described (4.8 g, 13.9 mmol) in toluene (10 ml) and stirred at reflux for 5 h. After cooling to room temperature, diethyl ether was added and the insoluble material removed by filtration. The organic fraction was then washed with water and extracted with dilute hydrochloric acid. The aqueous acidic fraction was subsequently basified with dilute sodium hydroxide to pH14 and extracted with diethyl ether (×2). The combined extracts were dried over sodium sulphate, filtered and the solvent removed under reduced pressure to give a yellow oil. Chromatography of this oil on alumina afforded the title compound (0.75 g).

Positive Ion ESI (M+H)+ 400.4

Example 5

5a: Propanedioic, (2-methoxyethyl)-, diethyl ester.

Sodium (8.4 g, 0.36 mol) was added portionwise with stirring to ethanol (400 ml) over 30 minutes. Once evolution of hydrogen had ceased, diethyl malonate (54.6 ml, 0.36 mol) was added slowly and the solution stirred for a further 30 minutes. 2-Bromoethyl methyl ether (50 g, 0.36 mol) was then added and the resultant solution heated at reflux with stirring under nitrogen for 4 h. A precipitate was evident after 1.5 h. The suspension was then allowed to cool to room temperature overnight and the precipitate removed by filtration. The solvent was removed under reduced pressure and the crude product dissolved in diethyl ether (200 ml) and washed with water (200 ml). The organic phase was then dried over sodium sulphate, filtered and concentrated under reduced pressure to give a yellow oil. The crude product was then purified by vacuum distillation (bp 84–86° C., 0.5 mmHg) to give the title compound (50 g, 64%) as a clear oil.

$^1$H NMR (CDCl$_3$): δ 1.27 (t, 6H), 2.16 (q, 2H), 3.31 (s, 3H), 3.41 (t, 2H), 3.52 (t, 1H), 4.20 (q, 4H).

The following compound was prepared in a similar manner:

5b: Propanedioic, (2-ethoxyethyl)-, diethyl ester.

$^1$H NMR (CDCl$_3$): δ 1.17 (t, 3H), 1.27 (t, 6H), 2.18 (q, 2H), 3.40–3.50 (m, 4H), 3.55 (t, 1H), 4.11–4.28 (m, 4H).

Example 6

6a: Propanedioic acid, (2-methoxyethyl)-.

Potassium hydroxide (61 g, 0.92 mol) was dissolved in 95/5 ethanol/water (400 ml) with stirring under nitrogen. Propanedioic, 2-methoxyethyl)-, diethyl ester (50 g, 0.23 mol) was then added and the resultant solution stirred at reflux overnight. The solution was then allowed to cool to room temperature and the solvent removed under reduced pressure. The residue was dissolved in a minimal amount of iced water and acidified to pH1 with 5N HCl. This solution was extracted with diethyl ether (250 ml ×3) and the combined ether fractions were dried over sodium sulphate, filtered and concentrated under reduced pressure to give the title compound (28.7 g, 77%) as a clear oil.

$^1$H NMR (CDCl$_3$): δ 1.21 (t, 1H), 2.19–2.29 (m, 1H), 3.35 (s, 3H), 3.47–3.56 (m, 2H), 3.61 (t, 1H).

The following compound was prepared in a similar manner:

6b: Propanedioic acid, (2-ethoxyethyl)-.

$^1$H NMR (CDCl$_3$): δ 1.10–1.31 (m, 4H), 2.18–2.26 (m, 1H), 3.39–3.64 (m, 4H), 3.66–3.79 (m, 1H).

Example 7

7a: 2-Bromo-4-methoxybutyric acid.

Propanedioic acid, (2-methoxyethyl)-(28.7 g, 0.18 mol) was dissolved in diethyl ether (300 ml) and three drops of 47% aqueous hydrobromic acid were added with stirring. Bromine (9.2 ml, 0.18 mol) was then added dropwise over minutes and the solution stirred at room temperature for a further 30 minutes. The solution was washed with dilute aqueous sodium metabisulphite, dried over sodium sulphate, filtered and concentrated under reduced pressure to give an orange oil (42 g). This oil was heated to 150° C. at atmospheric pressure for 30 minutes to effect decarboxylation. After cooling to 50° C., vacuum distillation (bp 104–106° C., 0.5 mmHg) afforded the title compound (19.2 g, 55%) as a clear viscous oil.

$^1$H NMR (CDCl$_3$): δ 2.14–2.24 (m, 1H), 2.32–2.45 (m, 1H), 3.36 (s, 3H), 3.52–3.61 (m, 2H), 4.46–4.52 (m, 1H).

The following compound was prepared in a similar manner:

7b: 2-Bromo-4-ethoxybutyric acid.

$^1$H NMR (CDCl$_3$): δ 1.19 (t, 3H), 2.12–2.27 (m, 1H), 2.32–2.42 (m, 1H), 3.44–3.55 (m, 2H), 3.56–3.64 (m, 2H), 4.45–4.53 (m, 1H).

Example 8

8a: 2-Bromo-4-methoxybutyryl chloride.

2-Bromo-4-methoxybutyric acid (19.2 g, 98 mmol) was dissolved in anhydrous dichloromethane and oxalyl chloride (10.2 ml, 117 mmol) added with stirring. One drop of pyridine was then added and the resultant solution stirred at room temperature overnight. The solvent and excess oxalyl chloride were removed under reduced pressure to give the title compound (20.4 g, 9 %) as a clear oil. This oil was used in subsequent reactions without further purification.

$^1$H NMR (CDCl$_3$): δ 2.16–2.30 (m, 1H), 2.40–2.52 (m, 1H), 3.35 (s, 3H), 3.51–3.60 (m, 2H), 4.70–4.80 (m, 1H).

The following compound was prepared in a similar manner:

8b: 2-Bromo-4-ethoxybutyryl chloride.

$^1$H NMR (CDCl$_3$): δ 1.19 (t, 3H), 2.19–2.29 (m, 1H), 2.41–2.52 (m, 1H), 3.41–3.52 (m, 2H), 3.53–3.64 (m, 2H), 3.71–3.80 (m, 1H).

Example 9

9a: 2-Bromo-4-methoxybutyric acid, 2,6-dimethoxyphenyl ester.

2-Bromo-4-methoxybutyryl chloride (10.7 g, 50 mmol) was dissolved in anhydrous dichloromethane and 2,6-dimethoxyphenol (8.4 g, 54 mmol) added. The resultant solution was then cooled using an ice bath and triethylamine (8.3 ml, 59 mmol) added dropwise over 30 minutes. The external cooling bath was then removed and the reaction mixture stirred at room temperature for a further 30 minutes. The solvent was removed under reduced pressure and diethyl ether (200 ml) added. The precipitate was removed by filtration and the filtrate washed with water (100 ml), dried over sodium sulphate, filtered and concentrated under reduced pressure, to give the title compound (15.2 g, 92%) as a viscous yellow oil.

$^1$H NMR (CDCl$_3$): δ 2.26–2.37 (m, 1H), 2.48–2.59 (m, 1H), 3.38 (s, 3H), 3.57–3.66 (m, 2H), 3.81 (s, 6H), 4.71–4.80 (m, 1H), 6.60 (d, 2H), 7.12 (t, 1H).

The following compounds were prepared in a similar manner:

9b: 2-Bromo-4-methoxybutyric acid, 2,6-dimethoxy-4-methylphenyl ester.

$^1$H NMR (CDCl$_3$): δ 2.26–2.36 (m, 4H), 2.48–2.59 (m, 1H), 3.37 (s, 3H), 3.55–3.63 (m, 2H), 3.78 (s, 6H), 4.69–4.78 (m, 1H), 6.40 (s, 2H).

9c: 2-Bromo-4-ethoxybutyric acid, 2,6-dimethoxyphenyl ester.

$^1$H NMR (CDCl$_3$): δ 1.21 (t, 3H), 2.26–2.37 (m, 1H), 2.47–2.59 (m, 1H), 3.51 (q, 2H), 3.61–3.69 (m, 2H), 3.80 (s, 6H), 4.71–4.80 (m, 1H), 6.62 (d, 2H), 7.13 (t, 1H).

9d: 2-Bromo-4-ethoxybutyric acid, 2,6-dimethoxy-4-methylphenyl ester.

$^1$H NMR (CDCl$_3$): δ 1.21 (t, 3H), 2.26–2.36 (m, 4H), 2.46–2.59 (m, 1H), 3.51 (q, 2H), 3.60–3.69 (m, 2H), 3.79 (s, 6H), 4.70–4.80 (m, 1H), 6.41 (s, 2H).

Example 10

10a: 2-[4-(Hexahydro-1-oxazepinyl)]-4-methoxybutyric acid, 2,6-dimethoxyphenyl ester.

2-Bromo-4-methoxybutyric acid, 2,6-dimethoxyphenyl ester (4.4 g, 13.3 mmol) was dissolved in toluene (30 ml). To this stirred solution was added triethylamine (4.6 ml, 33.3 mmol) and hexahydrooxazepine hydrochloride (1:1) salt (2.3 g, 16.7 mmol), and the reaction heated at 100° C. under nitrogen overnight. The reaction mixture was allowed to cool to room temperature and diluted. with diethyl ether (100 ml). The precipitate was removed by filtration and washed with diethyl ether (100 ml). The combined organic fractions were then extracted with 1N HCl (200 ml). The aqueous phase was subsequently basified to pH14 with 4M NaOH and extracted with diethyl ether (200 ml×2). The combined organic fractions were dried over sodium sulphate, filtered and concentrated under reduced pressure to give a yellow oil. Chromatography of this oil on basic alumina using toluene/ethyl acetate gradient as the eluent afforded the title compound (3.1 g, 64%) as a clear viscous oil.

$^1$H NMR (CDCl$_3$): δ 1.81–2.08 (m, 4H), 2.12–2.24 (m, 1H), 2.88–2.99 (m, 2H), 3.07–3.19 (m, 2H), 3.38 (s, 3H), 3.51–3.88 (m, 14H), 6.60 (d, 2H), 7.12 (t, 1H).

Positive Ion ESI (M+H)$^+$ 353.8

The following compounds were prepared in a similar manner:

10b: 4-Methoxy-2-[4-morpholinyl]butyric acid, 2,6-dimethoxyphenyl ester. Positive Ion ESI (M+H)$^+$ 339.8

10c: 4-Methoxy-2-[1-(1,2,3,6-tetrahydropyridinyl)]butyric acid, 2,6-dimethoxyphenyl ester: Positive Ion ESI (M+H)$^+$ 336.0

10d: 4-Methoxy-2-[1-(4-methoxypiperidinyl)]butyric acid, 2,6-dimethoxyphenyl ester: Positive Ion ESI (M+H)$^+$ 367.5

10e: 2-[1-(Hexahydroazepinyl)]-4-methoxybutyric acid, 2,6-dimethoxyphenyl ester: Positive Ion ESI (M+H)$^+$ 367.9

10f: 4-Methoxy-2-[1-piperidinyl]butyric acid, 2,6-dimethoxyphenyl ester. Positive Ion ESI (M+H)$^+$ 337.6

10g: 2-[N-(Bis(2-ethoxyethyl)amino)]-4-methoxybutyric acid, 2,6-dimethoxyphenyl ester: Positive Ion ESI (M+H)$^+$ 414.1

10h: 2-[N-(Bis(2-methoxyethyl)amino)]-4-methoxybutyric acid, 2,6-dimethoxyphenyl ester.

$^1$H NMR (CDCl$_3$): δ 1.92–2.03 (m, 1H), 2.15–2.24 (m, 1H), 2.97–3.03 (m, 4H), 3.35 (s, 6H), 3.37 (s, 3H), 3.45–3.51 (m, 4H), 3.55–3.70 (m, 2H), 3.79 (s, 6H), 3.84–3.91 (m, 1H), 6.60 (d, 2H), 7.12 (t, 1H).

Positive Ion ESI (M+H)+ 386.0

10i: 4-Methoxy-2-[4-morpholinyl]butyric acid, 2,6-dimethoxy-4-methylphenyl ester: Positive Ion ESI (M+H)+ 354.0

10j: 2-[4-(Hexahydro-1-oxazepinyl)]-4-methoxybutyric acid, 2,6-dimethoxy-4-methylphenyl ester: Positive Ion ESI (M+H)+ 368.0

10k: 4-Methoxy-2-[1-(4-methoxypiperidinyl)]butyric acid, 2,6-dimethoxy4-methylphenyl ester: Positive Ion ESI (M+H)+ 382.0

10l: 2-[N-(Bis(2-methoxyethyl)amino)]-4-methoxybutyric acid, 2,6-dimethoxy-4-methylphenyl ester.

$^1$H NMR (CDCl$_3$): δ 1.89–2.00 (m, 1H), 2.11–2.22 (m, 1H), 2.32 (s, 3H), 2.93–3.02 (m, 4H), 3.35 (s, 6H), 3.37 (s, 3H), 3.43–3.50 (m, 4H), 3.51–3.68 (m, 2H), 3.77 (s, 6H), 3.81–3.90 (m, 1H), 6.40 (s, 2H).

Positive Ion ESI (M+H)+ 400.1

10m: 2-[N-(Bis(2-ethoxyethyl)amino)]-4-methoxybutyric acid, 2,6-dimethoxy-4-methylphenyl ester.

$^1$H NMR (CDCl$_3$): δ 1.19 (t, 6H), 1.91–2.01 (m, 1H), 2.12–2.23 (m, 1H), 2.32 (s, 3H), 2.98 (t, 4H), 3.36 (s, 3H), 3.48–3.70 (m, 10H), 3.76 (s, 6H), 3.82–3.89 (m, 1H), 6.40 (s, 2H).

Positive Ion ESI (M+H)+ 428.3

10n: 2-[1-(Hexahydroazepinyl)]-4-methoxybutyric acid, 2,6-dimethoxy-4-methylphenyl ester: Positive Ion ESI (M+H)+ 365.9

10o: 4-Ethoxy-2-[4-morpholinyl]butyric acid, 2,6-dimethoxyphenyl ester.

Positive Ion ESI (M+H)+ 354.0

10p 4-Ethoxy-2-[4-(hexahydro-1-oxazepinyl)]butyric acid, 2,6-dimethoxyphenyl ester: Positive Ion ESI (M+H)+ 367.8

10q: 4-Ethoxy-2-[1-hexahydroazepinyl]butyric acid, 2,6-dimethoxyphenyl ester: Positive Ion ESI (M+H)+ 366.0

10r: 2-[N-(Bis(2-methoxyethyl)amino)]-4-ethoxybutyric acid, 2,6-dimethoxyphenyl ester.

$^1$H NMR (CDCl$_3$): δ 1.22 (t, 3H), 1.90–2.01 (m, 1H), 2.12–2.23 (m, 1H), 2.98 (t, 4H), 3.35 (s, 6H), 3.41–3.69 (m, 8H), 3.79 (s, 6H), 3.86 (dd, 1H), 6.60 (d, 2H), 7.10 (t, 1H).

Positive Ion ESI (M+H)+ 399.8

10s: 2-[N-(Bis(2-ethoxyethyl)amino)]-4-ethoxybutyric acid, 2,6-dimethoxyphenyl ester.

$^1$H NMR (CDCl$_3$): δ 1.13–1.25 (m, 9H), 1.90–2.02 (m, 1H), 2.11–2.23 (m, 1H), 2.93–3.02 (m, 4H), 3.46–3.56 (m, 10H), 3.57–3.71 (m, 2H), 3.79 (s, 6H), 3.89 (t, 1H), 6.59 (d, 2H), 7.10 (t, 1H).

Positive Ion ESI (M+H)+ 428.2

10t: 4-Ethoxy-2-[4-morpholinyl]butyric acid, 2,6-dimethoxy-4-methylphenyl ester: Positive Ion ESI (M+H)+ 367.8

10u: 4-Ethoxy-2-[1-hexahydroazepinyl]butyric acid, 2,6-dimethoxy-4-methylphenyl ester: Positive Ion ESI (M+H)+ 380.2

10v: 2-[N-(Bis(2-methoxyethyl)amino)]-4-ethoxybutyric acid, 2,6-dimethoxy-4-methylphenyl ester.

$^1$H NMR (CDCl$_3$): δ 1.22 (t, 3H), 1.87–1.99 (m, 1H), 2.10–2.22 (m, 1H), 2.32 (s, 3H), 2.98 (t, 4H), 3.35 (s, 6H), 3.41–3.69 (m, 8H), 3.76 (s, 6H), 3.84 (dd, 1H), 6.40 (s, 2H).

Positive Ion ESI (M+H)+ 413.8

10w: 4-Ethoxy-2-[4-(hexahydro-1-oxazepinyl)]butyric acid, 2,6-dimethoxy-4-methylphenyl ester: Positive Ion ESI (M+H)+ 382.2

Example 11

N-tert-Butoxycarbonyl-threonine, triethylamine salt.

Threonine (90 g, 0.76 mol) and triethylamine (157 ml, 1.13 mol) were dissolved in aqueous dioxan (1000 ml, 50:50 vol:vol) with stirring and 2-(tert-butoxycarbonyloxyimino)-2-phenylacetonitrile (204 g, 1.0 mol) was added. The reaction mixture was stirred at room temperature for 18 hours. The solvent was removed under reduced pressure to give a viscous yellow oil. The oil was dissolved in diethyl ether (500 ml), extracted with water (4×100 ml), and the aqueous extracts were combined and washed with diethyl ether (100 ml). The aqueous phase was concentrated under reduced pressure to give the title compound (214 g, 88%) as a viscous yellow oil.

$^1$H NMR (D$_2$O): δ 1.30 (d, 3H), 1.39 (t, 9H), 1.55 (s, 9H), 3.30 (q, 6H), 3.98–4.02 (m, 1H), 4.27–4.36 (m, 1H).

Example 12

N-tert-Butoxycarbonyl-threonine, sodium salt.

The triethylamine salt of N-tert-butoxycarbonyl-threonine (210 g, 066 mol) was dissolved in methanol (1500 ml) and sodium hydroxide pellets (26.4 g, 0.66 mol) were added with ice cooling. After 10 minutes the ice bath was removed and the reaction was stirred at room temperature until all the sodium hydroxide had dissolved. The solvent was then removed under reduced pressure to give a colourless gum which was triturated with ethyl acetate (400 ml) to give the title compound (164 g, quantitative yield) as a white solid.

$^1$H NMR (D$_2$O): δ 1.20 (d, 3H), 1.44 (s, 9H), 3.80–3.87 (m, 1H), 4.11–4.22 (m, 1H).

Example 13

N-tert-Butoxycarbonyl-O-methyl-threonine.

2-Propanol (60 ml, 0.78 mol) was dissolved in anhydrous tetrahydrofuran (150 ml) and sodium hydride (26.6 g, 0.665 mol, 60% dispersion in oil) was added portion wise at room temperature under a nitrogen atmosphere with stirring. The reaction mixture was cooled to 0° C. and the sodium salt of N-tert-butoxycarbonyl-threonine (40 g, 0.165 mol) was added portionwise followed by anhydrous tetrahydrofuran (450 ml) and stirred for 1.5 h. Iodomethane (69 ml, 1.1 mol) was dissolved in anhydrous tetrahydrofuran (500 ml) and added dropwise to the reaction mixture at such a rate as to maintain the temperature between 0° C. and 5° C. The reaction mixture was stirred at room temperature for 72 h then allowed to stand for 48 h. The solvent was removed under reduced pressure and the residue was dissolved in water (200 ml) and ethyl acetate (100 ml). The organic layer was removed and the aqueous phase was extracted with ethyl acetate (2×100 ml). The pH of the aqueous phase was adjusted to pH 4 with 2N HCl and extracted with ethyl acetate (3×100 ml). The organic extracts were combined and washed with water (100 ml), saturated sodium thiosulphate solution (100 ml) and finally saturated sodium chloride solution (100 ml). The organic solution was dried over sodium sulphate, filtered and evaporated under reduced pressure to give the title compound (4.69 g, 13%) as a pale yellow solid.

$^1$H NMR (CDCl$_3$): δ 1.21 (d, 3H), 1.47 (s, 9H), 3.39 (s, 3H), 3.94–4.03 (m, 1H), 4.34 (dd, 1H), 5.30 (d, 1H).

Example 14

2-Bromo-3-methoxybutanoic acid.

N-tert-Butoxycarbonyl-threonine (2 g, 8.6 mmol) was stirred in water (12 ml) and hydrobromic acid (7.96 ml, 68.8 mmol) and cooled to 0° C. Sodium nitrite was dissolved in water (10 ml) and added dropwise to the cooled reaction mixture. The reaction was stirred at room temperature for 18 h. The reaction mixture was poured into water (100 ml), extracted with diethyl ether (3×50 ml), and the organic extracts were combined and washed with saturated sodium metabisulphite solution (50 ml) followed by saturated sodium chloride. solution (50 ml). The diethyl ether was removed under reduced pressure to give the title compound (0.865 g, 50%) as a yellow oil.

$^1$H NMR (CDCl$_3$): δ 1.35 (d, 3H), 3.46 (s, 3H), 3.76–3.82 (m, 1H), 4.33 (d, 1H).

Example 15

2-Bromo-3-methoxybutyryl chloride.

2-Bromo-3-methoxybutanoic acid (0.865 g, 4.4 mmol) was dissolved in dichloromethane (15 ml) and cooled to 0° C. and oxalyl chloride (0.8 ml, 9.2 mmol) was added dropwise followed by one drop of pyridine (catalytic). The reaction mixture was stirred at room temperature for 18 h and the solvent was then removed under reduced pressure to give the title compound (0.944 g, 100%) as a yellow oil.

$^1$H NMR (CDCl$_3$): δ 1.37 (d, 3H), 3.42 (s, 3H), 3.89–3.97 (m, 1H), 4.60 (d, 1H).

Example 16

2-Bromo-3-methoxybutanoic acid, 2,6-dimethoxy-4-methylphenyl ester.

2-Bromo-3-methoxybutyryl chloride (0.944 g, 4.4 mmol) was dissolved in dichloromethane (20 ml) with 2,6-dimethoxy-4-methylphenol (0.740 g, 4.4 mmol) and cooled to 0° C. Triethylamine (0.64 ml, 4.6 mmol) was added dropwise at 0° C. and stirred at room temperature for 18 h. The reaction mixture was diluted with dichloromethane (100 ml), washed with water (3×50 ml) followed by saturated sodium chloride solution (50 ml), dried over sodium sulphate, filtered and evaporated under reduced pressure to give the title compound (1.32 g, 86%) as a yellow oil.

$^1$H NMR (CDCl$_3$): δ 1.41 (d, 3H), 2.33 (s, 3H), 3.50 (s, 3H), 3.80 (s, 6H), 3.85–3.95 (m, 1H), 4.48 (d, 1H), 6.40 (s, 2H).

Example 17

3-Methoxy-2-(4-morpholinyl)butanoic acid, 2,6-dimethoxy-4-methylphenyl ester.

Morpholine (0.66 ml, 7.6 mmol), was added to 2-bromo-3-methoxybutanoic acid, 2,6-dimethoxy-4-methylphenyl ester (1.32 g, 3.8 mmol) and heated to 100° C. for 5 h with stirring. The reaction mixture was diluted with diethyl ether (100 ml) and filtered. The filtrate was washed with water (50 ml) followed by 2N HCl (2×50 ml). The acidic extracts were combined and basified with 4N NaOH and extracted with diethyl ether (4×50 ml). The organic extracts were combined and washed with water (50 ml) followed by saturated sodium chloride solution (50 ml), dried over sodium sulphate, filtered and evaporated to give a brown oil, This was fractionated on Merck 7729 silica using a gradient elution from 95:5 petroleum ether:ethyl acetate to 80:20 petroleum ether:ethyl acetate to give the title compound (0.273 g, 20%) as a yellow oil.

Positive Ion ESI (M+H)$^+$ 353.8

Example 18

18a: 2,3-Di-(N-thiomorpholinyl)propanoic acid, 2,6-dimethoxyphenyl ester.

Thiomorpholine (1.8 ml, 19.1mmol) was added to a stirred solution of 2-bromoacrylic acid, 2,6-dimethoxyphenyl ester (2.5 g, 8.7 mmol) and triethylamine (3.6 ml, 26.1 mmol) in dichloromethane (3 ml). The resultant solution was stirred at room temperature for 1.5 h prior to the addition of diethyl ether. The precipitate was removed by filtration and the solvent removed under reduced pressure to give the crude product as an oil. Chromatography of this oil on alumina afforded the title compound (1.2 g)

Positive Ion ESI (M+H)$^+$ 413.5

The following compounds were prepared in a similar manner:

18b: 2,3-Di-[4-(2,2-dimethylmorpholinyl)]propanoic acid, 2,6-dimethoxyphenyl ester.

Positive Ion ESI (M+H)$^+$ 437.5

18c: 2,3-Di-(4-morpholinyl)propanoic acid, 2,6-dimethoxyphenyl ester.

$^1$H NMR (CDCl$_3$): δ 2.50–2.59 (m, 2H), 2.59–2.70 (m, 3H), 2.70–2.78 (m, 2H), 3.00–3.06 (m, 1H), 3.65–3.80 (m, 9H), 3.82 (s, 6H), 6.62 (d, 2H), 7.14 (t, 1H). Positive Ion ESI (M+H)$^+$ 381.1

Example 19

19a: 3-(4-Morpholinyl)-2-(N-thiomorpholinyl)propanoic acid, 2,6-dimethoxyphenyl ester.

Morpholine (5.3 ml, 60.6 mmol) was added to a solution of 2-bromoacrylic acid, 2,6-dimethoxyphenyl ester (17.4 g, 60.6 mmol) in dichloromethane (350 ml) and stirred at room temperature overnight. TLC analysis after this time showed complete consumption of 2-bromoacrylic acid, 2,6-dimethoxyphenyl ester. The solution was then concentrated under reduced pressure and carried forward without further purification. Thiomorpholine (0.45 ml) and diisopropylethylamine (2.1 ml) were added to a portion of the above intermediate in dichloromethane and stirred at room temperature overnight. The solvent was then removed under reduced pressure and diethyl ether added. The precipitate was removed by filtration and the solvent removed under reduced pressure to give the crude product as an oil. Chromatography of this oil on alumina afforded the title compound (0.64 g).

Positive Ion ESI (M+H)$^+$ 397.5

The following compounds were prepared in a similar manner:

19b: 3-(4-Morpholinyl)-2-(1,2,3,4-tetrahydroisoquinoline) propanoic acid, 2,6-dimethoxyphenyl ester: Positive Ion ESI (M+H)$^+$ 19c: 2-[N-(2,2-Dimethylthiomorpholinyl)]-3-(4-morpholinyl)propanoic acid, 2,6-dimethoxyphenyl ester: Positive Ion ESI (M+H)$^+$ 425.0

19d: 2-[(R)-4-(2-Methylmorpholinyl)]-3-(4-morpholinyl) propanoic acid, 2,6-dimethoxyphenyl ester: Positive Ion ESI (M+H)$^+$ 395.5

19e: 2-[(R)-4-(2-Ethylmorpholinyl)]-3-(4-morpholinyl)propanoic acid, 2,6-dimethoxyphenyl ester: Positive Ion ESI (M+H)+ 409.5

19f: 2-[4-(2-Ethyl-2-methylmorpholinyl)]-3-(4-morpholinyl)propanoic acid, 2,6-dimethoxyphenyl ester: Positive Ion ESI (M+H)+ 423.5

19g: 3-(4-Morpholinyl)-2-(1-piperidinyl)propanoic acid, 2,6-dimethoxyphenyl ester: Positive Ion ESI (M+H)+ 379.0

19h: 2-[(R)-Isopropylmorpholinyl)]-3-(4-morpholinyl)propanoic acid, 2,6-dimethoxyphenyl ester: Positive Ion ESI (M+H)+ 423.5

19i: 2-(4-Morpholinyl)-3-(N-thiomorpholinyl)propanoic acid, 2,6-dimethoxyphenyl ester: Positive Ion ESI (M+H)+ 397.0

19j: 2-(4-Morpholinyl)-3-(1,2,3,4-tetrahydroisoquinoline) propanoic acid, 2,6-dimethoxyphenyl ester: Positive Ion ESI (M+H)+ 427.0

19k: 3-(1,2,3,6-Tetrahydropyridinyl)-2-(N-thiomorpholinyl) propanoic acid, 2,6-dimethoxyphenyl ester: Positive Ion ESI (M+H)+ 393.5

Example 20

20a: Propanoic acid, 2,3-di(4-morpholinyl), 4-allyl-2,6-dimethoxyphenyl ester.
To a stirred solution of 4-allyl-2,6-dimethoxyphenol (3.5 g) and 2,3-dibromopropionyl chloride (4g) in dichloromethane (150 ml) was added triethylamine (5.6 ml) and stirring was continued for 24 h. The solvent was removed under reduced pressure and diethyl ether (100 ml) added. The suspension was filtered and the filtrate was concentrated under reduced pressure. To this was added dichloromethane (10 ml), triethylamine (6.7 ml), morpholine (3.5 ml) and the reaction mixture was stirred for 2 h. Chromatography on alumina gave the title compound (0.4 g, 6%) as an oil.
Positive ion ESI (M+H)+ 421

The following compounds were prepared in a similar manner:

20b: Propanoic acid, 2,3-di(4-morpholinyl), 2,6-diethoxyphenyl ester.
Positive ion ESI (M+H)+ 409

20c: Prorpanoic acid, 2,3-di(4-morpholinyl), 4-formyl-2,6-dimethoxyphenyl ester: Positive ion ESI (M+H)+ 409.5

20d: Propanoic acid, 2,3-di(4-morpholinyl), 2-allyl-6-methoxyphenyl ester.
Positive ion ESI (M+H)+ 391.5

Example 21

21a: 2,4-Di-(4-morpholinyl)butanoic acid, 2,6-dimethoxyphenyl ester.
Triethylamine (7 ml, 60 mmol) was added to a solution of tert-butyl-2,4-dibromobutyrate (3.2 ml, 16.6 mmol) in dichloromethane (minimum). Morpholine (3.2 ml, 36 mmol) was then added and the solution stirred at room temperature overnight. The solvent was removed under reduced pressure and ethyl acetate added. The solution was then washed with water and saturated brine, dried over sodium sulphate, filtered and the solvent removed under reduced pressure to give a yellow oil (3.1 g). The oil was dissolved in trifluoroacetic acid (10 ml) and dichloromethane (10 ml) and stirred at room temperature for 2.5 h. The solvent was removed under reduced pressure and any residual trifluoroacetic acid was azeotroped with dry toluene to give a yellow oil. The trifluoroacetate salt was then dissolved in dichloromethane (100 ml). To this solution was added diisopropylethylamine (5.7 ml, 32.7 mmol), 2,6-dimethoxyphenol (1.68 g, 10.9 mmol), PyBrOP (5.1 g, 10.9 mmol) and dimethylaminopyridine (cat) and the resultant solution stirred at room temperature for 3 h. The solvent was removed under reduced pressure and ethyl acetate added to give a suspension which was vigorously stirred for 15 minutes. Once the suspension had settled the ethyl acetate was decanted off and washed with water and saturated brine, dried over sodium sulphate, filtered and the solvent removed under reduced pressure to give an oil. Chromatography of this oil on alumina afforded the title compound (0.45 g).
$^1$H NMR (CDCl$_3$): δ 1.90–1.99 (m, 1H), 2.06–2.16 (m, 1H), 2.40–2.61 (m, 6H), 2.70–2.78 (m, 2H), 2.85–2.95 (m, 2H), 3.52–3.62 (m, 1H), 3.70–3.80 (m, 8H), 3.82 (s, 6H), 6.61 (d, 2H), 7.13 (t, 1H).
Positive Ion ESI (M+H)+ 395.5
The following compound was prepared in a similar manner:

21b: 2,4-Di-[(4-(2,2-dimethylmorpholinyl)]butanoic acid, 2,6-dimethoxyphenyl ester: Positive Ion ESI (M+H)+ 451.4

Example 22

2-Butenedioic acid (2Z)-, monomethyl ester.
A solution of maleic anhydride (30 g) in methanol (200 ml) was heated to reflux for 0.5 h. The reaction mixture was allowed to cool and was then concentrated under reduced pressure to give the title compound (39 g, 98%) as a clear oil. $^1$H NMR (CDCl$_3$); δ 3.91 (s, 3H), 6.39 (d, 1H), 6.46 (d, 1H)

Example 23

Butanedioic, 2-[N-bis(2-methoxyethyl)amino]-, 4-methyl ester, sodium salt.
A mixture of 2-butenedioic acid (2Z)-, monomethyl ester (23 g) and bis(2-methoxyethyl)amine (80 ml) were heated, under nitrogen, at 130° C. for 1 h. The reaction mixture was allowed to cool to room temperature and the excess bis(2-methoxyethyl)amine removed under high vacuum. The resulting oil was redissolved in methanol (300 ml) and sodium hydroxide (7.1 g) was added. The suspension was stirred for 2 h and then concentrated under reduced pressure to give the title compound (48 g, 95%) as a brown oil.
Positive ion ESI (M+H)+ 264.1

Example 24

24a: Butanedioic, 2-[N-bis(2-methoxyethyl)amino]-, 1-(2,6-dimethoxyphenyl)ester, 4-methyl ester.
To butanedioic, 2-[N-bis(2-methoxyethyl)amino]-, 4-methyl ester, sodium salt (13 g) was added 2,6-dimethoxyphenol (10.6 g), dichloromethane (100 ml), 4-dimethylaminopyridine (5.6 g), triethylamine (12.7 ml) and 1-(3-dimethylaminopropyl)-3-ethylcarbodiimide hydrochloride (13.1 g). The resulting suspension was stirred overnight and was then chromatographed on silica gel to give the title compound (2 g, 11%) as a brown oil.
Positive ion ESI (M+H)+ 400.2
The following compound was prepared in a similar manner:

24b: Butanedioic, 2-[N-bis(2-methoxyethyl)amino]-, 1-(2,6-dimethoxy-4-methylphenyl)ester, 4-methyl ester: Positive ion ESI (M+H)$^+$ 414.2

Example 25

Butanedioic acid, 2-(4-morpholinyl)-, 4-methyl ester, sodium salt.
A solution of maleic anhydride (25.3 g) in methanol (100 ml) was heated at reflux for 0.5 h with stirring. Once the reaction mixture had cooled to room temperature morpholine (67.5 ml) was added and stirring-was continued for 1 h. To this mixture was added sodium hydroxide (10.3 g) and the suspension was stirred for 1 h. The reaction mixture was concentrated under reduced pressure and the resulting solid was filtered and washed with ethyl acetate (300 ml) to give the title compound (52.9 g, 86%).
Positive ion ESI (M+H)$^+$ 218.2

Example 26

26a: Butanedioic, 2-(4-morpholinyl)-, 1-(2,6-dimethoxyphenyl)ester, 4-methyl ester.
To butanedioic acid, 2-(4-morpholinyl)-, 4-methyl ester, sodium salt (13 g) was added 2,6-dimethoxyphenol (8.0 g), chloroform (100 ml), 4-dimethylaminopyridine (4.3 g), triethylamine (9.7 ml) and 1-(3-dimethylaminopropyl)-3-ethylcarbodiimide hydrochloride (10 g). The resulting suspension was stirred overnight then chromatographed on silica gel. The resulting solid was washed with petroleum ether (100 ml) to give the title compound (5 g, 41%) as a white solid. Positive ion ESI (M+H)$^+$ 353.8
The following compound was prepared in a similar manner:
26b: Butanedioic, 2-(4-morpholinyl)-, 1-(2,6-dimethoxy-4-methylphenyl)ester, 4-methyl ester: Positive ion ESI (M+H)$^+$ 368.0

Example 27

Butanedioic acid, 2-(1-piperidinyl)-, 4-methyl ester, sodium salt.
A solution of maleic anhydride (25.3 g) in methanol (100 ml) was heated at reflux for 0.5 h, with stirring, then was cooled to 0° C. with an ice/acetone bath. Piperidine (67.5 ml) was added and the reaction mixture was heated to 50° C. for 1 h. Sodium hydroxide (9.2 g) was added and the suspension was stirred for 1 h. The reaction mixture was concentrated under reduced pressure and the resulting solid. was filtered and washed with ethyl acetate (300 ml) to give the title compound (43 g, 79%) as a white solid.
Positive ion ESI (M+H)$^+$ 230.0

Example 28

28a: Butanedioic, 2-(1-piperidinyl)-, 1-(2,6-dimethoxyphenyl)ester, 4-methyl ester.
To butanedioic acid, 2-(1-piperidinyl)-, 4-methyl ester, sodium salt (10 g) was added 2,6-dimethoxyphenol (8.5 g), dichloromethane (100 ml), 4-dimethylaminopyridine (5.2 g), triethylamine (11.7 ml) and 1-(3-dimethylaminopropyl)-3-ethylcarbodiimide hydrochloride (10.5 g). The resulting suspension was stirred overnight then chromatographed on silica gel. The resulting solid was washed with diethyl ether (100 ml) to give the title compound (3.3 g, 22%) as a white solid. Positive ion ESI (M+H)$^+$ 352.0
The following compound was prepared in a similar manner.
28b: Butanedioic, 2-(1-piperidinyl)-, 1-(2,6-dimethoxy-4-methylphenyl)ester, 4-methyl ester: Positive ion ESI (M+H)$^+$ 366

Example 29

Butanedioic acid, 2-(1-hexahydroazepinyl)-, 4-methyl ester, sodium salt.
A solution of maleic anhydride (20 g) in methanol (200 ml) was heated at reflux for 0.5 h, with stirring, then was cooled to 20° C. Hexamethyleneimine (67.5 ml) was added dropwise and the temperature was maintained at 20° C. After complete addition the reaction mixture was stirred for 1 h at room temperature. Sodium hydroxide (8.2 g) was added and stirring was continued for 1 h. The reaction mixture was concentrated under reduced pressure and dichloromethane (300 ml) was added. The suspension was filtered and the filtrate was concentrated under reduced pressure to give the title compound (37 g, 72%) as an orange oil.
Positive ion ESI (M+H)$^+$ 230.0

Example 30

30a: Butanedioic, 2-(1-hexahydroazepinyl)-, 1-(2,6-dimethoxyphenyl)ester, 4-methyl ester.
To butanedioic acid, 2-(1-hexahydroazepinyl)-, 4-methyl ester, sodium salt (11.7 g) was added 2,6-dimethoxyphenol (9.3 g), dichloromethane (100 ml), 4-dimethylaminopyridine (5.7 g), triethylamine (13 ml) and 1-(3-dimethylaminopropyl)-3-ethylcarbodiimide
hydrochloride (11.6 g). The resulting mixture was stirred for 72 h then chromatographed on silica gel to give the title compound (7.1 g, 42%) as a clear oil.
Positive ion ESI (M+H)$^+$ 365.6
The following compound was prepared in a similar manner:
30b: Butanedioic, 2-(1-hexahydroazepinyl)-, 1-(2,6-dimethoxy-4-methyl-phenyl)ester, 4-methyl ester: Positive ion ESI (M+H)$^+$ 379.8

Example 31

Butanedioic, 4-(diethylamino)-4-oxo-, 2-(4-morpholinyl)-, sodium salt.
To a suspension of maleic anhydride (20 g) in dichloromethane (300 ml) at 0° C. was added a solution of diethylamine (19.4 ml) in dichloromethane (100 ml). The reaction mixture was allowed to warm to room temperature and concentrated under reduced pressure. Methanol (300 ml) was added followed by morpholine (71.2 ml) and the resulting mixture heated at reflux for 3 h. The reaction mixture was allowed to cool to room temperature. Sodium hydroxide (8.16 g) was added and the suspension stirred for 1 h. Concentration under reduced pressure gave an oil which solidified on stirring with petroleum ether (300 ml). The solid was filtered to give the title compound (47 g, 82%) as a white solid. Positive ion ESI (M+H)$^+$ 259.0

Example 32

Butanedioic, 4-(diethylamino)-4-oxo-, 2-(4-morpholinyl)-, 1-(2,6-dimethoxy4-methylphenyl)ester.

To butanedioic, 4-(diethylamino)4-oxo-, 2-(4-morpholinyl)-, sodium salt (10 g) was added 2,6-dimethoxy-4-methylphenol (7.8 g), chloroform (100 ml), 4-dimethylaminopyridine (0.5 g), triethylamine (10 ml) and PyBroP (21.6 g). The resulting suspension was stirred overnight then chromatographed on silica gel to give the title compound (5 g, 34%) as a white foam. Positive ion ESI (M+H)$^+$ 409.4

Example 33

Butanedioic, 4-(1-piperidinyl)-4-oxo-, 2-(1-piperidinyl)-, sodium salt.

To a suspension of maleic anhydride (20 g) in dichloromethane (200 ml) at 0° C. was added a solution of piperidine (40.3 ml) in dichloromethane (100 ml). The reaction mixture was allowed to warm to room temperature and concentrated under reduced pressure. Methanol (200 ml) was added followed by piperidine (40.3 ml) and the resulting mixture heated at reflux for 3 h. The reaction mixture was allowed to cool to room temperature. Sodium hydroxide (8.2 g) was added and the suspension stirred for 1 h. Concentration under reduced pressure then stirring with diethyl ether (300 ml) gave a solid which was filtered to give the title compound (34 g, 58%) as a white solid.
Positive ion ESI (M+H)$^+$ 269.2

Example 34

34a: Butanedioic, 4-(1-piperidinyl)-4-oxo-, 2-(1-piperidinyl)-, 1-(2,6-dimethoxy-4-methylphenyl)ester.

To butanedioic, 4-(1-piperidinyl)-4-oxo-, 2-(1-piperidinyl)-, sodium salt (11.2 g) was added 2,6-dimethoxy-4-methylphenol (7.9 g), chloroform (150 ml), 4-dimethylaminopyridine (4.8 g), triethylamine (10.9 ml) and 1-(3-dimethylaminopropyl)-3-ethylcarbodiimide hydrochloride (9 g). The resulting suspension was stirred overnight then chromatographed on silica gel to give the title compound (4 g, 24%) as a clear oil. Positive ion ESI (M+H)$^+$ 419.2

The following compound was prepared in a similar manner:

34b: Butanedioic, 4-(1-piperidinyl)-4-oxo-, 2-(1-piperidinyl)-1-(2,6-dimethoxyphenyl)ester: Positive ion ESI (M+H)$^+$ 405.4

Example 35

Butanedioic, 2-(1-hexahydroazepinyl)-4-oxo-4-(1-pyrrolidinyl)-, sodium salt.

To a suspension of maleic anhydride (24.4 g) in dichloromethane (300 ml) at 0° C. was added a solution of pyrrolidine (20.8 ml) in dichloromethane (150 ml). The reaction mixture was allowed to warm to room temperature and concentrated under reduced pressure. Methanol (250 ml) was added followed by hexamethyleneimine (84.2 ml) and the resulting mixture heated at reflux for 3 h. The reaction mixture was allowed to cool to room temperature. Sodium hydroxide (9.96 g) was added and the suspension heated at 60° C. for 1 h. Concentration under reduced pressure gave a solid which was stirred with diethyl ether (300 ml). The solid was filtered to give the title compound (57 g, 79%) as a white solid. Positive ion ESI (M+H)$^+$ 269.0

Example 36

Butanedioic, 2-(1-hexahydroazepinyl)-4-oxo-4-(1-pyrrolidinyl)-, 1-(2,6-dimethoxyphenyl)ester.

To butanedioic, 2-(1-hexahydroazepinyl)-4-oxo-4-(1-pyrrolidinyl)-, sodium salt (11.4 g) was added 2,6-dimethoxyphenol (7.2 g), chloroform (150 ml), 4-dimethylaminopyridine (4.8 g), triethylamine (10.9 ml) and 1-(3-dimethylaminopropyl)-3-ethylcarbodiimide hydrochloride (9 g). The resulting suspension was stirred overnight then chromatographed on silica gel. Recrystallisation from ethyl acetate gave the title compound (4.5 g, 28%) as white crystals.
Positive ion ESI (M+H)$^+$ 405.4

Example 37

Butanoic acid, 2-bromo-4-(methylthio)-.

To a stirred solution of methionine (85.4 g) in water (792 ml) and hydrobromic acid (47% aqueous, 528 ml) at 0° C. was added a solution of sodium nitrite (39.5 g) in water (100 ml). Stirring was continued for 2 h at 0° C. and the reaction allowed to warm to room temperature and stand for 24 h. The aqueous phase was extracted with ethyl acetate (500 ml), dried (sodium sulphate), filtered and concentrated under reduced pressure to give the title compound (33 g, 27%) as an orange oil.
$^1$H NMR (CDCl$_3$); δ 2.11 (3H, s), 2.17–2.42 (2H, m), 2.58–2.70 (2H, m), 4.88–4.45 (1H, m)

Example 38

38a: Butanoic acid, 2-bromo-4-(methylthio), 1-(2,6-dimethoxyphenyl)ester.

To a solution of butanoic acid, 2-bromo-4-(methylthio)- (33 g) and pyridine (0.5 ml) in dichloromethane (50 ml) was added a solution of oxalyl chloride (27 ml) in dichloromethane (50 ml). The reaction mixture was stirred for 24 h and concentrated under reduced pressure. To this solution was added dichloromethane (100 ml) and 2,6-dimethoxyphenol (23.9 g) and the reaction mixture was cooled to 0° C. A solution of triethylamine (43 ml) in dichloromethane (50 ml) was then added. dropwise. After complete addition the reaction mixture was allowed to warm to room temperature and stirred for 2 h. Concentration under reduced pressure and chromatography on silica gel gave the title compound (25.8 g, 48%) as an orange oil.
$^1$H NMR (CDCl$_3$); δ 2.15 (s, 3H), 2.33–2.43 (m, 1H), 2.48–2.58 (m, 1H), 2.72–2.79 (m, 2H), 3.82 (s, 6H), 4.71–4.75 (t, 1H), 6.60 (d, 2H), 7.02 (t, 1H)

The following compound was prepared in a similar manner:

38b: Butanoic acid, 2-bromo-4-(methylthio), 1-(2,6-dimethoxy-4-methylphenyl)ester.
$^1$H NMR (CDCl$_3$); δ 2.14 (s, 3H), 2.33 (s, 3H), 2.36–2.45 (m, 1H), 2.50–2.58 (m, 1H), 2.72–2.76 (m, 2H), 3.79 (s, 6H), 4.71 (t, 1H), 6.41 (s, 2H)

Example 39

39a: Butanoic acid, 4-(methylthio)-2-(4-morpholinyl)-, 1-(2,6-dimethoxy-4-methylphenyl)ester.
Butanoic acid, 2-bromo-4-(methylthio), 1-(2,6-dimethoxy-4-methylphenyl)ester (5.4 g) and morpholine (5.2 ml) were heated at 35° C. for 2 h. Chromatography on silica gel gave the title compound (1 g, 19%) as an oil.
Positive ion ESI (M+H)$^+$ 353.8

The following compounds were prepared in a similar manner:

39b: Butanoic acid, 4-(methylthio)-2-(1-pyrrolidinyl)-, 1-(2,6-dimethoxy-4-methylphenyl)ester: Positive ion ESI (M+H)$^+$ 353.8

39c: Butanoic acid, 2-[N-bis(2-methoxyethyl)amino]-4-(methylthio), 1-(2,6-dimethoxy-4-methylphenyl)ester: Positive ion ESI (M+H)$^+$ 416.2

Example 40

40a: Butanoic acid, 4-(methylthio)-2-(1-piperidinyl)-, 1-(2,6-dimethoxyphenyl)ester.
Butanoic acid, 2-bromo-4-(methylthio), 1-(2,6-dimethoxyphenyl)ester (5 g) and piperidine (5.2 ml) were stirred together for 1 h. Chromatography on silica gel gave the title compound (1.3 g, 26%) as a solid.
Positive ion ESI (M+H)$^+$ 353.8

The following compounds were prepared in a similar manner:

40b: Butanoic acid, 4-(methylthio)-2-(1-pyrrolidinyl)-, 1-(2,6-dimethoxyphenyl)ester: Positive ion ESI (M+H)$^+$ 339.4

40c: Butanoic acid, 2-(1-hexahydroazepinyl)-4-(methylthio), 1-(2,6-dimethoxyphenyl)ester: Positive ion ESI (M+H)$^+$ 367.8

40d: Butanoic acid, 2-(1-hexahydroazocinyl)-4-(methylthio), 1-(2,6-dimethoxyphenyl)ester: Positive ion ESI (M+H)$^+$ 382.2

Example 41

Butanoic acid, 2-bromo-4-(methylsulphonyl)-
To a stirred solution of methionine (42.7 g) in water (396 ml) and hydrobromic acid (47% aqueous, 264 ml) at 0° C. was added a solution of sodium nitrite (63.2 g) in water (200 ml). Stirring was continued for 2 h at 0° C. and then the reaction was allowed to warm to room temperature and stand for 24 h. After addition of sodium metabisulphite (10 g), the aqueous phase was extracted with ethyl acetate (500 ml), dried (sodium sulphate), filtered and concentrated under reduced pressure to give the title compound (33 g, 47%) as a pale yellow solid. Negative ion ESI (M–H)$^-$ 244.6

Example 42

Butanoic acid, 2-bromo-4-(methylsulphonyl), 1-(2,6-dimethoxy-4-methylphenyl)ester.
To a solution of butanoic acid, 2-bromo-4-(methylsulphonyl)-(5.4 g) and pyridine (0.2 ml) in dichloromethane (50 ml) was added oxalyl chloride (3.9 ml). The reaction mixture was stirred for 24 h and concentrated under reduced pressure. To this mixture was added dichloromethane (50 ml) and 2,6-dimethoxy-4-methylphenol (4.8 g). Triethylamine (6.1 ml) was then added dropwise. After complete addition the reaction mixture was allowed to stir for 2 h. Chromatography on silica gel gave the title compound (7 g, 80%) as a solid. Negative ion ESI (M–H)$^{31}$ 394.4

Example 43

Butanoic acid, 4-(methylsulphonyl)-2-(1-[1,2,3,6-tetrahydropyridinyl])-, 1-(2,6-dimethoxy-4-methylphenyl)ester.
Butanoic acid, 2-bromo-4-(methylsulphonyl), 1-(2,6-dimethoxy-4-methylphenyl)ester (3.2 g) and 1,2,3,6-tetrahydropyridine (3 ml) were stirred together for 2 h. Chromatography on silica gel gave the title compound (1 g, 31%) a solid. Positive ion ESI (M+H)$^+$ 398.0

Example 44

2-Bromopentane-1,5-dioic acid, mono-5-methyl ester.
An aqueous solution of sodium nitrite (10.5 g, 0.15 mol in 25 ml H$_2$O) was added dropwise to a stirred solution of L-glutamate 5-methyl ester (8.06 g, 0.05 mol) in aqueous HBr (47%, 47 ml) and water (70 ml) cooled to −5° C. in an ice/acetone bath. The sodium nitrite solution was added over 1 h with care being taken to maintain the temperature at <0° C. After an additional 1 h, the aqueous solution was washed with diethylether (3×150 ml). The combined organic phase was then washed with saturated sodium metabisulfite solution (2×75 ml) until the bromine colour was removed. The organic phase was dried (Na$_2$SO$_4$), filtered and solvent removed to give the title compound as a yellow oil (7.47 g, 66.4%).
$^1$H NMR (CDCl$_3$): δ 4.47–4.40 (m, 1H), 3.70 (s, 3H), 2.60–2.54 (m, 2H), 2.47–2.37 (m, 1H), 2.37–2.24 (m, 1H).

Example 45

2-Bromopentan-1-oylchloride, mono-5-methyl ester.
Oxalyl chloride (12.21 ml, 0.14 mol) was added dropwise over 1 h under nitrogen to a stirred solution of 2-bromopentane-1,5-dioic acid, mono-5-methyl ester (15.86 g, 0.07 mol) in dichloromethane (300 ml) and pyridine (3 drops), cooled in an ice bath. The reaction was allowed to warm slowly to room temperature and stirring continued overnight. After 17 h $^1$H nmr showed that the reaction was incomplete so more oxalyl chloride (8.00 ml, 1.31 eq.) was added. After 22 h, the solvent was removed in vacuo to give the title compound as a yellow oil (19.08 g, 100%). This intermediate was used directly without further purification.
$^1$H NMR (CDCl$_3$): δ 4.72 (dd, 1H), 3.72 (s, 3H), 2.60–2.45 (m, 3H), 2.37–2.28 (m, 1H)

Example 46

46a: Pentanedioic acid, 2-bromo-, 1-(2,6-dimethoxyphenyl) ester, 5-methyl ester.
Triethylamine (14.17 ml, 0.10 mol) was added slowly, under nitrogen, to a stirred solution of 2-bromopentan-1-oylchloride mono-5-methyl ester (12.00 g, 0.046 mol) and 2,6-dimethoxyphenol (8.55 g, 0.055 mol) in dichloromethane (100 ml) cooled in an ice bath. The system was then allowed to warm to room temperature and stirring continued for 6 h whereupon solvent was removed in vacuo. The residue was dissolved in water (50 ml) and extracted with diethylether (2×200 ml). The combined organic phase was dried (Na$_2$SO$_4$), filtered and the solvent removed to give the crude product as a dark brown oil. This was purified by chromatography on alumina (pet. ether:EtOAc, 2:1) to give the title compound as a clear oil (12.96 g, 77.7%).

$^1$H NMR (CDCl$_3$): δ 7.14 (dd, 1H), 6.60 (d, 2H), 4.65 (dd, 1H), 3.82 (s, 6H), 3.72 (s, 3H), 2.68–2.62 (m, 2H), 2.61–2.42 (m, 2H).

The following compound was prepared in a similar manner:

46b: Pentanedioic acid, 2-bromo-, 1-(2,6-dimethoxy-4-methylphenyl)ester, 5-methyl ester.

$^1$H NMR (CDCl$_3$): δ 6.41 (2H, s), 4.63 (1H, dd), 3.79 (6H, s), 3.71 (3H, s), 2.69–2.62 (2H, m), 2.62–2.40 (2H, m), 2.34 (3H, s).

Example 47

47a: Pentanedioic acid, 2-(1-piperidinyl)-, 1-(2,6-dimethoxyphenyl)ester, 5-methyl ester hydrochloride (1:1) salt.

Piperidine (1.69 ml, 0.017 mol) and pentanedioic acid, 2-bromo-, 1-(2,6-dimethoxyphenyl)ester, 5-methyl ester (2.06 g, 5.71 mmol) were stirred together neat at room temperature for 18 h. Chromatography of the residue on alumina (pet. ether:ethyl acetate 4:1) gave the desired product as a clear oil (0.61 g, 29%). Hydrogen chloride gas was bubbled through a solution of the product in diethylether and the white precipitate that formed was collected by filtration and dried under vacuum (0.48 g).

$^1$H NMR (CDCl$_3$+Na$_2$CO$_3$): δ1.53–1.43 (m, 2H), 1.68–1.53 (m, 4H), 2.15 (q, 2H), 2.59–2.46 (m, 2H), 2.68–2.59 (m, 2H), 2.88–2.79 (m, 2H), 3.47 (dd, 1H), 3.70 (s, 3H), 3.81 (s, 6H), 6.60 (d, 2H), 7.10 (dd, 1H).

Positive ion ESI (M+H)$^+$ 366; ν/cm (KBr) 3440, 2950, 2319, 1758, 1731, 1609, 1482.

The following compounds were prepared in a similar manner:

47b: Pentanedioic acid, 2-(1-hexahydroazepinyl)-, 1-(2,6-dimethoxyphenyl)ester, 5-methyl ester hydrochloride (1:1) salt.

$^1$H NMR (CDCl$_3$+Na$_2$CO$_3$): δ 1.74–1.52 (m, 8H), 2.27–2.03 (m, 2H), 2.58 (dd, 2H), 2.84–2.72 (m, 2H), 3.05–2.95 (m, 2H), 3.60 (dd, 1H), 3.70 (s, 3H), 3.80 (s, 6H), 6.60 (d, 2H), 7.10 (dd, 1H).

Positive ion ESI (M+H)$^+$ 380
ν/cm (KBr) 3440, 2936, 2423, 1760, 1732, 1608, 1483.

47c: Pentanedioic acid, 2-(N-thiomorpholinyl)-, 1-(2,6-dimethoxyphenyl)ester, 5-methyl ester hydrochloride (1:1) salt $^1$H NMR (CDCl$_3$+Na$_2$CO$_3$): δ 2.20–2.11 (m, 2H), 2.60–2.42 (m, 2H), 2.76–2.60 (m, 4H), 3.00–2.90 (m, 2H), 3.23–3.14 (m, 2H), 3.49 (dd, 1H), 3.70 (s, 3H), 3.83 (s, 6H), 6.60 (d, 2H), 7.12 (dd, 1H).

Positive ion ESI (M+H)$^+$ 384
ν/cm (KBr) 2962, 2298, 1761, 1728, 1610, 1484.

Example 48

48a: Pentanedioic acid, 2-[bis-(2-methoxyethyl)amino]-, 1-(2,6-dimethoxyphenyl)ester, 5-methyl ester hydrochloride (1:1) salt.

Bis-(2-methoxyethyl)amine (2.53 ml, 0.017 mol) and pentanedioic acid, 2-bromo-, 1-(2,6-dimethoxyphenyl)ester, 5-methyl ester (2.06 g, 5.71 mmol) were stirred together neat at room temperature for 18 h and then at 60° C. for a further 6 h. The residue was dissolved in dichloromethane and extracted with 1M HCl. The aqueous phase was then neutralised using solid sodium bicarbonate and the solution was extracted with diethylether (3×100 ml). The combined organic layer was dried (Na$_2$SO$_4$), filtered and the solvent removed in vacuo. Chromatography of the residue on alumina (pet. ether:ethyl acetate, 3:1) gave the desired product as a clear oil (1.63 g, 69%). Hydrogen chloride gas was bubbled through a solution of the product in diethylether and the white precipitate that formed was collected by filtration and dried under vacuum (1.12 g). $^1$H NMR (CDCl$_3$+Na$_2$CO$_3$): δ 2.11–2.00 (m, 1H) 2.31–2.19 (m, 1H), 2.69–2.52 (m, 2H), 3.02–2.94 (m, 4H), 3.35 (s, 6H), 3.52–3.39 (m, 4H), 3.70 (s, 3H), 3.79–3.74 (m, 1H), 3.80 (s, 6H), 6.60 (d, 2H), 7.11 (dd, 1H).

Positive ion ESI (M+H)$^+$ 414
ν/cm (KBr) 3430, 2944, 2139, 1749, 1739, 1619, 1485.

Example 49

49a: Pentanedioic acid, 2-(1-pyrrolidinyl)-, 1-(2,6-dimethoxy4-methylphenyl)-ester, 5-methyl ester hydrochloride (1:1) salt.

Pyrrolidine (1.23 ml, 0.015 mol) and pentanedioic acid, 2-bromo-, 1-(2,6-dimethoxy-4-methylphenyl)ester, 5-methyl ester (1.85 g, 4.93 mmol) were stirred together at room temperature for 18 h. Chromatography on alumina (pet. ether:ethyl acetate, 2:1) gave the desired product as a clear oil (0.35 g, 19.4%). Hydrogen chloride gas was bubbled through a solution of the product in diethylether and the white precipitate that formed was collected by filtration and dried under vacuum (0.22 g).

$^1$H NMR (CDCl$_3$+Na$_2$CO$_3$): δ 1.88–1.78 (m, 4H) 2.28–2.20 (m, 2H), 2.33 (s, 3H), 2.70–2.49 (m, 2H), 2.86–2.78 (m, 4H), 3.48 (dd, 1H), 3.69 (s, 3H), 3.77 (s, 6H), 6.41 (s, 2H).

Positive ion ESI (M+H)$^+$ 366
ν/cm (KBr) 3397, 2944, 2586, 1767, 1739, 1605, 1506, 1418.

The following compounds were prepared in a similar manner:

49b: Pentanedioic acid, 2-(1-piperidinyl)-, 1-(2,6-dimethoxy-4-methylphenyl)ester, 5-methyl ester hydrochloride (1:1) salt.

$^1$H NMR (CDCl$_3$+Na$_2$CO$_3$): δ 1.67–1.42 (m, 6H), 2.21–2.12 (m, 2H), 2.33 (s, 3H), 2.59–2.46 (m, 2H), 2.67–2.59 (m, 2H), 2.86–2.78 (m, 2H), 3.44 (dd, 1H), 3.69 (s, 3H), 3.78 (s, 6H), 6.41 (s, 2H).

Positive ion ESI (M+H)$^+$ 380
ν/cm (KBr) 3440, 2923, 2246, 1755, 1732, 1605, 1506, 1455.

49c: Pentanedioic acid, 2-(N-thiomorpholinyl)-, 1-(2,6-dimethoxy-4-methylphenyl)ester, 5-methyl ester hydrochloride (1:1) salt.

$^1$H NMR (CDCl$_3$+Na$_2$CO$_3$): δ 2.17–2.08 (m, 2H), 2.34 (s, 3H), 2.58–2.42 (m, 2H), 2.74–2.60 (m, 4H), 2.98–2.89 (m, 2H), 3.21–3.12 (m, 2H), 3.50–3.42 (m, 1H), 3.70 (s, 3H), 3.80 (s, 6H), 6.42 (s, 2H).

Positive ion ESI (M+H)$^+$ 398
ν/cm (KBr) 3444, 2949, 2253, 1764, 1736, 1606, 1507, 1467.

Example 50

Pentanedioic acid, 2-[N-bis(2-ethoxyethyl)amino)]-, 1-(2,6-dimethoxy-4-methylphenyl)ester, 5-methyl ester hydrochloride (1:1) salt.

Bis(2-ethoxyethyl)amine (2.90 ml, 0.017 mol) and pentanedioic acid, 2-bromo-, 1-(2,6-dimethoxy-4-methylphenyl)ester, 5-methyl ester (2.00 g, 5.33 mmol)

were stirred together neat at room temperature for 18 h and then at 60° C. for a further 4 h. Chromatography of the residue on alumina (pet. ether:ethyl acetate, 3:1) gave the desired product as a clear oil (1.45 g, 60%). Hydrogen chloride gas was bubbled through a solution of the product in diethylether and the white precipitate that formed was collected by filtration and dried under vacuum (1.05 g).

$^1$H NMR (CDCl$_3$+Na$_2$CO$_3$): δ 1.20 (t, 6H), 2.12–2.01 (m, 1H), 2.28–2.17 (m, 1H), 2.33 (s, 3H), 2.72–2.51 (m, 2H), 3.01–2.94 (m, 4H), 3.54–3.44 (m, 8H), 3.69 (s, 3H), 3.76–3.71 (m, 1H), 3.77 (s, 6H), 6.40 (s, 2H).

Positive ion ESI (M+H)$^+$ 456 v/cm (KBr) 3443, 2970, 2127, 1759, 1732, 1604, 1507, 1464.

Example 51

51a: (ξ)-2-[4-(Hexahydro-1-oxazepinyl)]-4-methoxybutyric acid,2,6-dimethoxyphenyl ester.

The racemic 2-[4-(hexahydro-1-oxazepinyl)]-4-methoxybutyric acid, 2,6-dimethoxyphenyl ester, described previously, was resolved via chiral preparative chromatography on a Chiracel OJ column (2 cm×25 cm, Daicel) using isohexane-isopropanol (97:3 v/v) as the eluent. The title compound eluted second. Positive Ion ESI (M+H)$^+$ 354.1

The following compounds were prepared in a similar manner. In some instances a different ratio of isohexane to isopropanol was used and diethylamine (HPLC grade) could also be added (0.1%).

51b: (ξ)-2-[4-(Hexahydro-1-oxazepinyl)]-4-methoxybutyric acid,2,6-dimethoxyphenyl ester. (1$^{st}$ to elute)
Positive Ion ESI (M+H)$^+$ 354.1

51c: (ξ)-2-[N-Bis(2-methoxyethyl)amino]-3-methoxypropionic acid, 2,6-dimethoxy-4-methylphenyl ester. (1$^{st}$ to elute)
Positive Ion ESI (M+H)$^+$ 386.4

51d: (ξ)-2-[N-Bis(2-methoxyethyl)amino]-3-methoxypropionic acid, 2,6-dimethoxy-4-methylphenyl ester. (2$^{nd}$ to elute)
Positive Ion ESI (M+H)$^+$ 386.4

51e: (ξ)-3-(4-Morpholinyl)-2-(N-thiomorpholinyl)propanoic acid, 2,6-dimethoxyphenyl ester. (1$^{st}$ to elute)
Positive Ion ESI (M+H)$^+$ 397.0

51f: (ξ)-3-(4-Morpholinyl)-2-(N-thiomorpholinyl)propanoic acid, 2,6-dimethoxyphenyl ester. (2$^{nd}$ to elute);
Positive Ion ESI (M+H)$^+$ 397.0

Example 52

52a: 2R-[4-(Hexahydro-1-oxazepinyl)]-3-methoxypropionic acid, 2,6-dimethoxyphenyl ester.

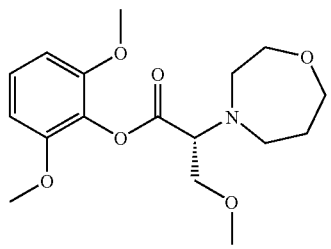

The racemic 2-[4-(hexahydro-1-oxazepinyl)]-3-methoxypropionic acid, 2,6-dimethoxyphenyl ester ,described previously, (30 g, 88 mmol) was dissolved in ethyl acetate and a solution of di-p-toluoyl-R-tartaric acid in ethyl acetate (300 ml) added. When crystallisation was complete the salt was filtered off, washed and dried (20.3 g). This salt was converted to the free base using sodium bicarbonate solution and ethyl acetate giving the free base as a clear oil (9.6 g). Analysis by liquid chromatography (Chiracel OJ) as described previously showed 82% of the required isomer (second to elute). This process was then repeated on the partly purified base, until after three further treatments analysis showed 99% of the required isomer (4.85 g).

Positive ion ESI (M+H)$^+$ 339.9

The following compound was prepared in a similar manner using di-p-toluoyl-S-tartaric acid:

52b: 2S-[4-(Hexahyro-1-oxazepinyl)]-3-methoxypropionic acid ,2,6-dimethoxyphenyl ester (1$^{st}$ to elute)
Positive ion ESI (M+H)$^+$ 339.9

The following enantiomers were prepared in a similar manner:

52c: (ξ)-2-[4-(Hexahydro-1-oxazepinyl)]-3-ethoxypropionic acid, 2,6-dimethoxyphenyl ester (2$^{nd}$ isomer to elute)
Positive ion ESI (M+H)$^+$ 353.7

52d: (ξ)-2-[4-Hexahydro-1-oxazepinyl)]-3-ethoxypropionic acid, 2,6-dimethoxyphenyl ester (1$^{st}$ isomer to elute)
Positive ion ESI (M+H)$^+$ 353.7

Example 53

2-[4-(Hexahydro-1-oxazepinyl)]-3-methoxypropionic acid, 2,6-dimethoxyphenyl ester hydrochloride (1:1) salt.

Hydrogen chloride gas was passed through a solution of 2-[4-(hexahydro-1-oxazepinyl)]-3-methoxypropionic acid, 2,6-dimethoxyphenyl ester (0.7 g) in anhydrous dichloromethane for 1–2 minutes. Most of the dichloromethane was then removed under reduced pressure and the hydrochloride salt precipitated by the addition of dry diethyl ether. The resulting white solid was filtered off and washed with diethyl ether to give the title compound (0.7 g, 90%). $^1$H NMR (CDCl$_3$+sodium carbonate): δ 1.85–2.02 (m, 2H), 2.95–3.04 (m, 2H), 3.05–3.17 (m, 2H), 3.43 (s, 3H), 3.67–3.87 (m, 12H), 3.93 (t, 1H), 6.60 (d, 2H), 7.13 (t, 1H). Positive Ion ESI (M+H)$^+$ 339.9

Example 54

54a: 2R-[4-(Hexahydro-1-oxazepinyl)]-3-methoxypropionic acid,2,6-dimethoxyphenyl ester hydrobromide (1:1) salt.

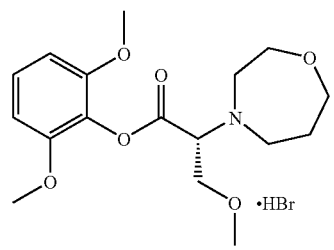

2R-[4-(Hexahydro-1-oxazepinyl)]-3-methoxypropionic acid, 2,6-dimethoxyphenyl ester (4.75 g) was dissolved in dry diethyl ether and hydrogen bromide gas bubbled in with cooling till a slight excess was present. The crystals were filtered off, washed and dried to give the title compound (5.57 g). A sample was crystallised from a mixture of methanol and isopropanol to give a single crystal. X-ray crystal structure analysis showed this to be the RR isomer.

$^1$H NMR (CDCl$_3$+sodium carbonate) δ 1.85–1.99 (m, 2H), 2.95–3.02 (m, 2H), 3.02–3.16 (m, 2H), 3.43 (s, 3H), 3.81 (s, 6H), 3.70–3.92 (m, 7H), 6.60 (d, 2H), 7.11 (t, 1H). Positive ion ESI (M+H)$^+$ 339.6

The following compound was prepared in a similar manner:

54b: 2S-[4-(Hexahydro-1-oxazepinyl)]-3-methoxypropionic acid, 2,6-dimethoxyphenyl ester hydrobromide 1;1 salt.

$^1$H NMR (CDCl$_3$) δ 1.85–1.99 (m, 2H), 2.95–3.02 (m, 2H), 3.02–3.16 (m, 2H), 3.43 (s, 3H), 3.81 (s, 6H), 3.70–3.92 (m, 7H), 6.60 (d, 2H), 7.11 (t, 1H); Positive ion ESI (M+H)$^+$ 339.7

Example 55

Hypnotic Activity

The hypnotic potency of the alanine 2,6-dialkoxyphenyl ester derivatives of the invention was determined upon their intravenous administration in mice. The dose required to cause a loss of righting reflex for a minimum period of 30 seconds in 50% of treated mice after intravenous injection over 10 seconds was determined. This dose is termed the HD$_{50}$ (hypnotic dose$_{50}$) and is expressed in μmol.kg$^{-1}$. These in vivo experiments were carried out as described in detail by Anderson et al., J. Med. Chem. 1997, 40, 1668–1681. The in vivo HD$_{50}$ data for a number of compounds of the invention are given in Table I.

The in vitro effect of the compounds of the invention at GABA$_A$ receptors was assessed through determination of their ability to inhibit [$^{35}$S]-TBPS ([$^{35}$S]-tert-butyl bicyclophosphorothionate) binding to rat whole brain membranes. The concentration of alanine 2,6-dialkoxyphenyl ester derivative required to inhibit 50% of binding of [$^{35}$S]-TBPS, i.e. the IC$_{50}$, was determined. These in vitro experiments were carried out as described in detail by Anderson et al., J. Med. Chem. 1997, 40, 1668–1681.

TABLE 1

| | | | | Hypnotic Activity | | | |
|---|---|---|---|---|---|---|---|
| Example | HD50 μmol·kg$^{-1}$ | Example | HD50 μmol·kg$^{-1}$ | Example | HD50 μmol·kg$^{-1}$ | Example | HD50 μmol·kg$^{-1}$ |
| 3a | 30 | 10h | 27 | 19g | 15 | 40b | 40 |
| 3b | 41 | 10i | 36 | 19h | 21 | 40c | 18 |
| 3c | 21 | 10j | 25 | 19i | 19 | 40d | 35 |
| 3d | 22 | 10k | 34 | 19j | 21 | 43 | 39 |
| 3f | 46 | 10l | 26 | 19k | 15 | 47a | 50 |
| 3g | 25 | 10m | 25 | 20b | 24 | 47b | 36 |
| 3i | 28 | 10n | 38 | 21a | 50 | 47c | 44 |
| 3j | 42 | 10o | 36 | 21b | 25 | 48 | 37 |
| 3l | 58 | 10p | 23 | 24a | 48 | 49a | 50 |
| 3m | 31 | 10q | 25 | 24b | 48 | 49b | 47 |
| 3n | 34 | 10r | 27 | 26b | 46 | 50 | 40 |
| 3p | 46 | 10s | 47 | 28a | 26 | 51a | 15 |
| 3q | 23 | 10t | 36 | 28b | 48 | 51b | 30 |
| 3r | 20 | 10u | 17 | 30a | 23 | 51c | 24 |
| 4a | 28 | 10v | 41 | 30b | 26 | 51d | 36 |
| 10a | 15 | 10w | 26 | 32a | 38 | 52a | 16 |
| 10b | 38 | 18a | 15 | 34a | 38 | 52b | 40 |
| 10c | 22 | 18b | 31 | 34b | 39 | | |
| 10d | 21 | 18c | 31 | 36 | 34 | | |

TABLE 1-continued

| | | | | Hypnotic Activity | | | |
|---|---|---|---|---|---|---|---|
| Example | HD50 μmol·kg$^{-1}$ | Example | HD50 μmol·kg$^{-1}$ | Example | HD50 μmol·kg$^{-1}$ | Example | HD50 μmol·kg$^{-1}$ |
| 10e | 17 | 19a | 17 | 39a | 35 | | |
| 10f | 22 | 19b | 29 | 39b | 31 | | |
| 10g | 28 | 19c | 28 | 39c | 23 | | |
| | | 19d | 27 | 40a | <26 | | |
| | | 19e | 27 | | | | |
| | | 19f | 21 | | | | |

The invention claimed is:

1. An alanine 2,6-dialkoxyphenyl ester derivative having the general formula I

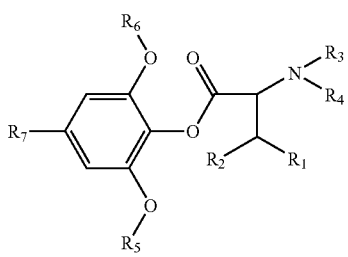

Formula I wherein
R$_1$ is (C$_{1-3}$)alkyloxy, (C$_{1-3}$)alkyloxy(C$_{1-3}$)alkyl, (C$_{1-3}$)alkylthio, (C$_{1-3}$)alkylthio(C$_{1-3}$)alkyl, (C$_{1-3}$)alkylsulfinyl, (C$_{1-3}$)alkylsulfinyl(C$_{1-3}$)alkyl, (C$_{1-3}$)alkylsulfonyl, (C$_{1-3}$)alkylsulfonyl(C$_{1-3}$)alkyl, (C$_{1-3}$)alkyloxycarbonyl, (CH$_2$)$_n$—CO—NR$_8$R$_9$ or (CH$_2$)$_n$—NR$_8$R$_9$;
n is 0, 1 or 2;
R$_2$ is hydrogen or (C$_{1-3}$)alkyl;
R$_3$ is (C$_{1-3}$)alkyl or (C$_{1-3}$)alkyloxy(C$_{1-3}$)alkyl;
R$_4$ is (C$_{1-3}$)alkyloxy(C$_{1-3}$)alkyl; or
R$_3$ and R$_4$ form together with the nitrogen atom to which they are bound a 5-, 6-, or 7-membered ring, optionally containing a further heteroatom selected from O and S, and which ring may optionally contain a double bond and be optionally substituted with (C$_{1-3}$)alkyl or (C$_{1-3}$)alkyloxy;
R$_5$ and R$_6$ are independently (C$_{1-3}$)alkyl;
R$_7$ is hydrogen, (C$_{1-3}$)alkyl, (C$_{1-3}$)alkyloxy or (C$_{2-3}$)alkenyl;
R$_8$ and R$_9$ are independently (C$_{1-3}$)alkyl; or
R$_8$ and R$_9$ form together with the nitrogen atom to which they are bound a 5-, 6-, or 7-membered, optionally containing a further heteroatom selected from O and S, and which ring may optionally contain a double bond; or a pharmaceutically acceptable salt thereof.

2. The alanine 2,6-dialkoxyphenyl ester derivative of claim 1, wherein R$_5$ and R$_6$ are methyl.

3. The alanine 2,6-dialkoxyphenyl ester derivative of claim 1, wherein R$_3$ and R$_4$ form together with the nitrogen atom to which they are bound a 5-, 6- or 7-membered ring, optionally containing a further heteroatom selected from O and S, and which ring may optionally contain a double bond and be optionally substituted with (C$_{1-3}$)alkyl or (C$_{1-3}$)alkyloxy.

4. The alanine 2,6-dialkoxyphenyl ester derivative of claim 3, wherein R$_1$ is (C$_{1-3}$)alkyloxy or (C$_{1-3}$)alkyloxy(C$_{1-3}$)alkyl.

5. The alanine 2,6-dialkoxyphenyl ester derivative of claim 4, wherein the α-carbon atom is that of the R-enantiomer.

6. A pharmaceutical composition, comprising:
an alanine 2,6-dialkoxyphenyl ester derivative according to claim 1, or a pharmaceutically acceptable salt thereof, and
pharmaceutically acceptable auxiliaries.

7. A method of manufacturing a pharmaceutical composition, comprising:
admixing the alanine 2,6-dialkoxyphenyl ester derivative according to claim 1, or a pharmaceutically acceptable salt thereof, and
pharmaceutically acceptable auxiliaries.

8. A method of treating GABA related diseases selected from the group consisting of anxiety, stress, sleep disorders, post natal depression, and premenstrual tension, in a patient in need thereof, comprising:
administering to a patient in the need thereof an effective amount of the alanine 2,6-dialkoxyphenyl ester derivative according to claim 1, or a pharmaceutically acceptable salt.

9. The method according to claim 8, wherein an administration route is selected from the group consisting of oral, sublingual, subcutaneous, intravenous, intramuscular, and rectal.

10. A method of inducing hypnotic activity in a patient, comprising:
administering to a patient an effective amount of the 2,6-dialkoxyphenyl ester derivative according to claim 1, wherein the effective amount induces hypnotics.

11. The method according to claim 10, wherein an administration route is selected from the group consisting of oral, sublingual, subcutaneous, intravenous, intramuscular, and rectal.

12. A method to induce analgesic activity in a patient in need thereof, comprising:
administering to a patient an effective amount of the 2,6-dialkoxyphenyl ester derivative according to claim 1, wherein the effective amount induces analgesic activity in said patient.

13. The method according to claim 12, wherein an administration route is selected from the group consisting of oral, sublingual, subcutaneous, intravenous, intramuscular, and rectal.

14. The method according to claim 12, wherein the administration route is intravenous.

* * * * *

UNITED STATES PATENT AND TRADEMARK OFFICE
CERTIFICATE OF CORRECTION

PATENT NO. : 7,141,560 B2
APPLICATION NO. : 10/466805
DATED : November 28, 2006
INVENTOR(S) : Niall Morton Hamilton and David Jonathan Bennett It is certified that error appears in the above-identified patent and that said Letters Patent is hereby corrected as shown below:

Claim 1, Column 28, line 53:

"a further heteroatom selected from O and S, and which"     should read

--a further heteroatom selected from ring O and S, and which--

Claim 8, Column 29, line 22:

"salt."     should read

--salt thereof.--

Signed and Sealed this

Twenty-fourth Day of April, 2007

JON W. DUDAS
*Director of the United States Patent and Trademark Office*